United States Patent
Hiroshima et al.

(10) Patent No.: US 12,076,192 B2
(45) Date of Patent: Sep. 3, 2024

(54) ULTRASOUND IMAGING DEVICE, SIGNAL PROCESSING DEVICE, AND SIGNAL PROCESSING METHOD

(71) Applicant: FUJIFILM Healthcare Corporation, Kashiwa (JP)

(72) Inventors: Misaki Hiroshima, Chiba (JP); Nobuhiko Fujii, Chiba (JP)

(73) Assignee: FUJIFILM Healthcare Corporation, Chiba (JP)

( * ) Notice: Subject to any disclaimer, the term of this patent is extended or adjusted under 35 U.S.C. 154(b) by 0 days.

(21) Appl. No.: 17/719,672

(22) Filed: Apr. 13, 2022

(65) Prior Publication Data

US 2022/0338843 A1    Oct. 27, 2022

(30) Foreign Application Priority Data

Apr. 27, 2021    (JP) ................. 2021-075205

(51) Int. Cl.
*A61B 8/00*    (2006.01)
*A61B 8/08*    (2006.01)
(Continued)

(52) U.S. Cl.
CPC .......... *A61B 8/5269* (2013.01); *A61B 8/4488* (2013.01); *A61B 8/483* (2013.01); *G01S 7/52077* (2013.01); *G01S 15/8915* (2013.01)

(58) Field of Classification Search
CPC ..... A61B 8/5269; A61B 8/4488; A61B 8/483; A61B 8/5207; A61B 8/54; A61B 8/085;
(Continued)

(56) References Cited

U.S. PATENT DOCUMENTS

2003/0011285 A1*    1/2003    Ossmann ............ G01S 7/52079
                                                              310/334
2005/0228279 A1*    10/2005    Ustuner .............. G01S 15/8927
                                                              600/443
(Continued)

FOREIGN PATENT DOCUMENTS

JP    2015-173728 A    10/2015
JP    2018-134275 A     8/2018
(Continued)

OTHER PUBLICATIONS

David Napolitano, et al., Sound speed correction in ultrasound imaging, Ultrasonics, vol. 44, ISSN 0041-624X, pp. 43-46, 2006 (Year: 2006).*

(Continued)

*Primary Examiner* — Alexei Bykhovski
(74) *Attorney, Agent, or Firm* — Paul Teng

(57) ABSTRACT

A coherence indicator of received signals is calculated for pixels with a small amount of calculation, and a high-quality ultrasound image is obtained. A plurality of types of images in which a sound speed for beamforming is changed into a plurality of types are generated. By arranging, in order of the sound speed for beamforming, signal intensities of the pixels at corresponding positions between the plurality of types of images, a change in signal intensities in a direction of the sound speed for beamforming is obtained. A coherence indicator representing coherence of the received signals used for beamforming of the pixels is calculated based on the obtained change in the signal intensities.

21 Claims, 17 Drawing Sheets

(51) Int. Cl.
  *G01S 7/52* (2006.01)
  *G01S 15/89* (2006.01)
(58) Field of Classification Search
  CPC ......... A61B 8/44; A61B 8/461; A61B 8/5215; G01S 7/52077; G01S 15/8915; G01S 15/8993; G01S 7/52049
  See application file for complete search history.

(56) References Cited

U.S. PATENT DOCUMENTS

2013/0253325 A1* 9/2013 Call ..................... A61B 8/5246
                                                       600/447
2015/0073276 A1   3/2015 Napolitano et al.

FOREIGN PATENT DOCUMENTS

| JP | 2020-137876 A | | 9/2020 |
| WO | WO2015087227 | * | 6/2015 |
| WO | WO2020/070104 A1 | | 4/2020 |

OTHER PUBLICATIONS

David Napolitano, et al., "Sound speed correction in ultrasound imaging", Ultrasonics, vol. 44, ISSN 0041-624X, pp. 43-46, 2006.
Stine M. Hverven, et al., "The Influence of Speckle Statistics on Contrast Methods in Ultrasound Imaging", IEEE International Ultrasounds Symposium (IUS), Washington, DC, pp. 1-4, 2017.
Japanese official action dated Dec. 19, 2023 (and English translation thereof) in Connection with corresponding Japanese Patent Application No. 2021-075205.

* cited by examiner (a) IN CASE OF DELAY TIME CALCULATED AT OPTIMUM SOUND SPEED

IN CASE OF DELAY TIME CALCULATED AT SOUND SPEED SLOWER THAN OPTIMUM SOUND SPEED

PIXEL WITH HIGH COHERENCE
(SUCH AS STRUCTURE IN IMAGING TARGET)

——— QUADRATIC APPROXIMATION
········· CUBIC APPROXIMATION

PIXEL WITH LOW COHERENCE
(SUCH AS ARTIFACT COMPONENT AND NOISE COMPONENT)

——— QUADRATIC APPROXIMATION
········· CUBIC APPROXIMATION

FIG. 5A
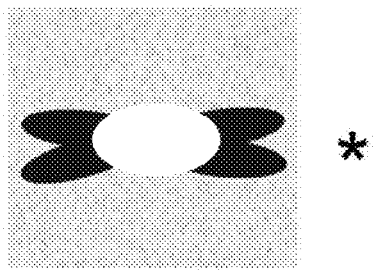
COHERENCE
INDICATOR IN ROI
*
FIG. 5B
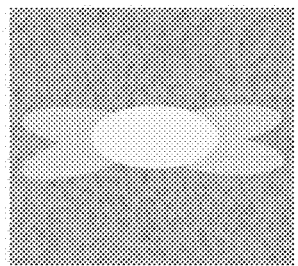
SIGNAL INTENSITY
(BRIGHTNESS VALUE)
IN ROI
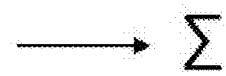
TOTAL SUM OR
AVERAGE VALUE
IN ROI (= FOCUS
INDICATOR)
FIG. 5C
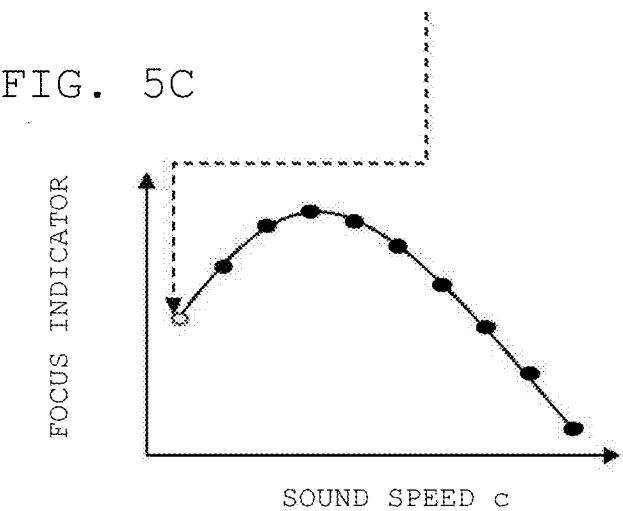

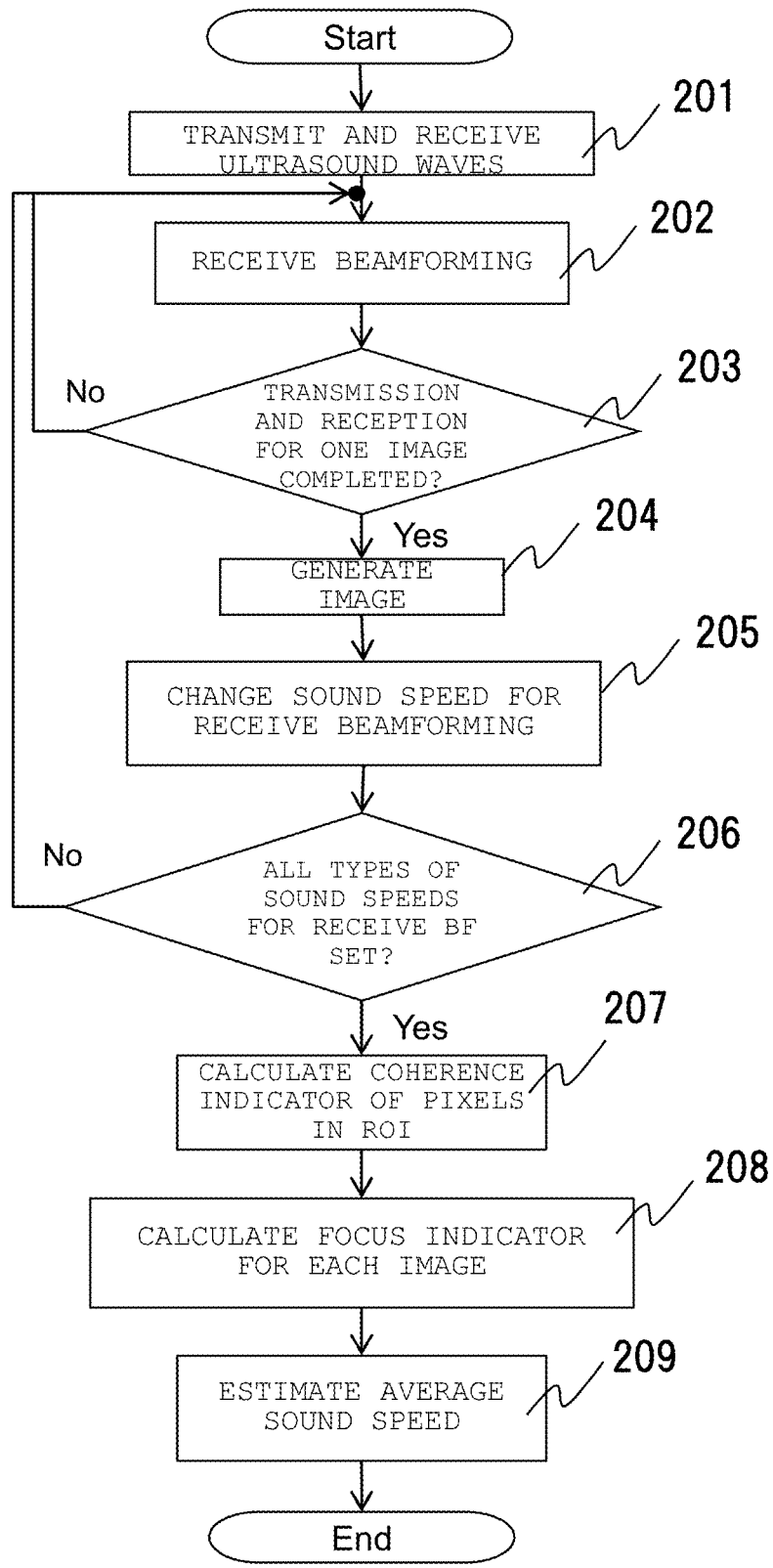

FIG. 8A
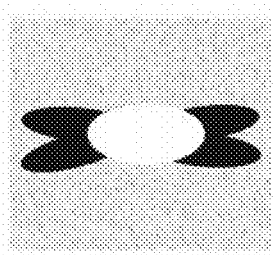
DISTRIBUTION OF
COHERENCE INDICATORS
IN ROI
FIG. 8B
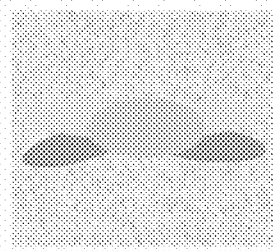
DISTRIBUTION OF SOUND
SPEED AT WHICH MAXIMUM
SIGNAL INTENSITY IS
OBTAINED IN ROI
→ AVERAGE VALUE OF
SOUND SPEED
WEIGHTED BY
COHERENCE VALUE
IN ROI

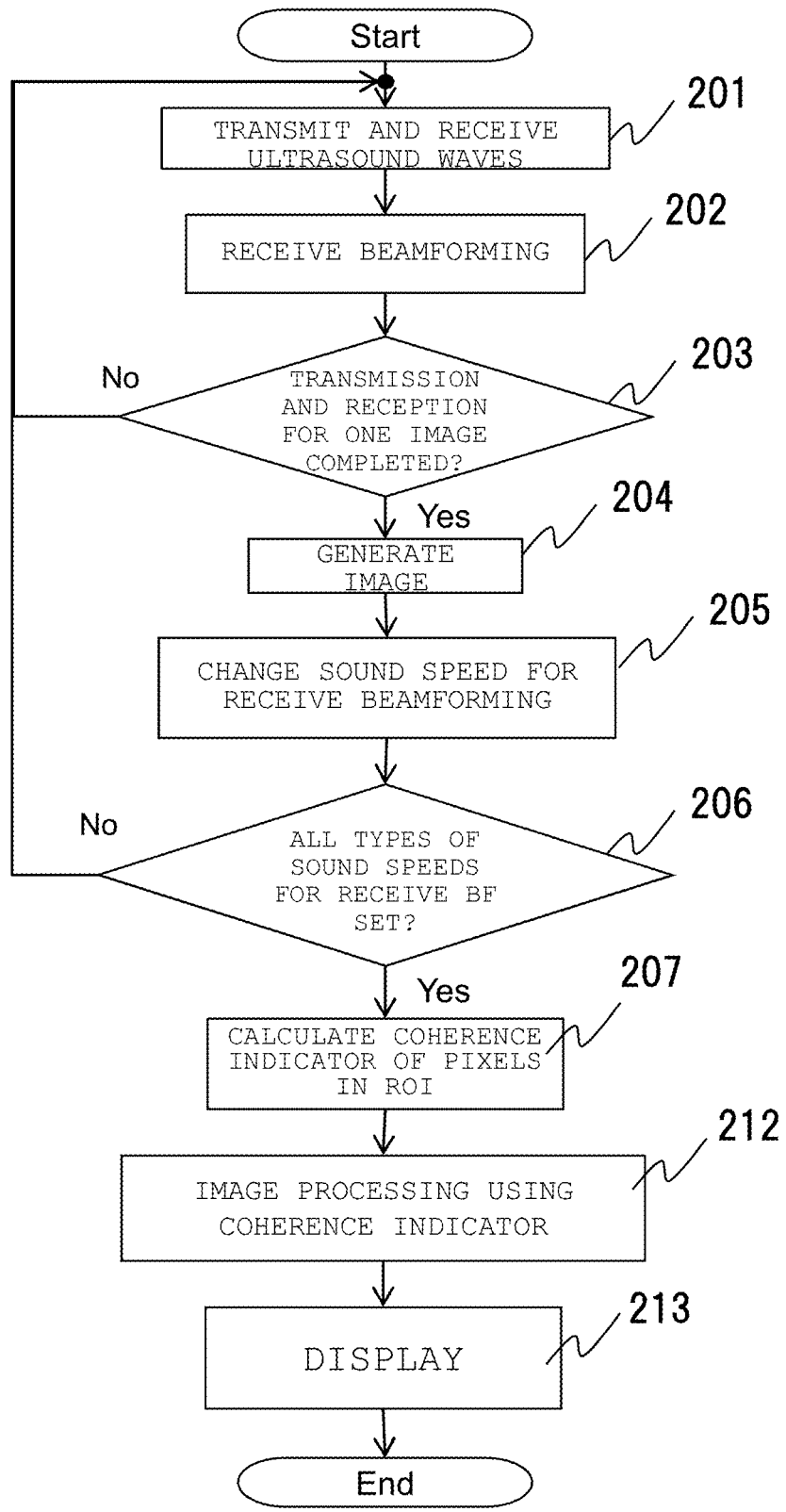

FIG. 16A
FIRST IMAGE (SOUND SPEED $C_0$)
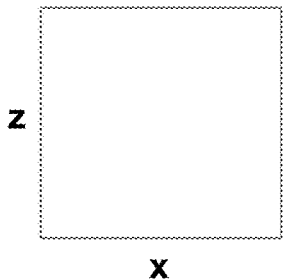
2DFFT
FIG. 16B
FIRST WAVENUMBER SPACE DATA (SOUND SPEED $C_0$)
k-k SPACE
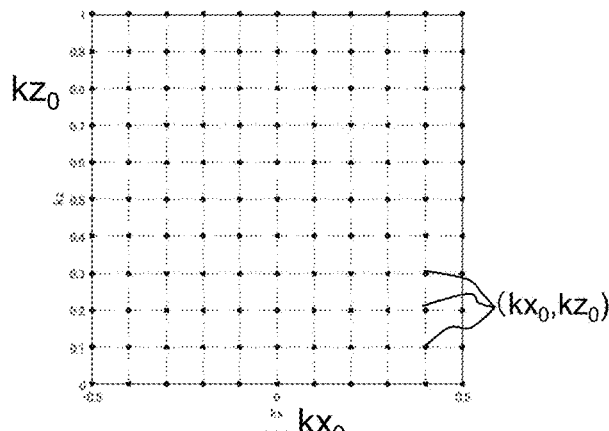
$kz_0$
$(kx_0, kz_0)$
$kx_0$
FIG. 16C
INTERPOLATION OF FIRST WAVENUMBER SPACE DATA (SOUND SPEED $C_0$)
k-k SPACE
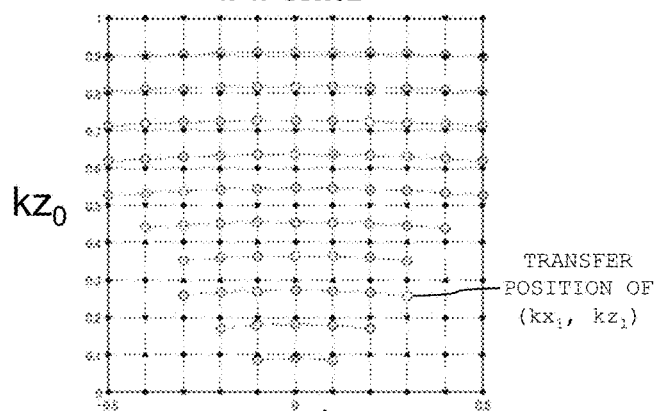
$kz_0$
TRANSFER POSITION OF $(kx_1, kz_1)$
$kx_0$
FIG. 16D
SECOND WAVENUMBER SPACE DATA (SOUND SPEED $C_1$)
k-k SPACE
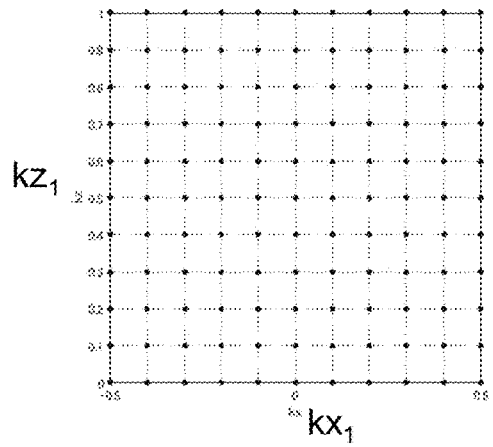
$kz_1$
$kx_1$
FIG. 16E
SECOND ACTUAL SPACE IMAGE (SOUND SPEED $C_1$)
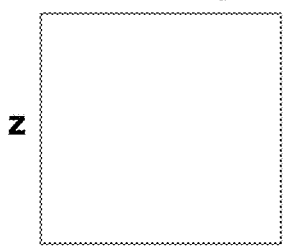
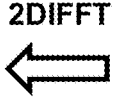
2DIFFT

ULTRASOUND IMAGING DEVICE, SIGNAL PROCESSING DEVICE, AND SIGNAL PROCESSING METHOD

BACKGROUND OF THE INVENTION

Technical Field

The present disclosure relates to an ultrasound imaging device.

Background Art

A sound speed in a living body varies depending on tissues such as fat and muscles, and also has individual differences. An ultrasound imaging device transmits ultrasound waves from an ultrasound probe element row toward the living body, receives echo signals generated in the living body, and performs receive beamforming processing in which the obtained received signals (channel RF signals) are delayed by delay times corresponding to distances between reception focal points and ultrasound probe elements and then are added. In general, the delay times at the time of receive beamforming are calculated using an average value, which is set in advance, or the like of sound speeds of the ultrasound waves propagating in the living body. However, when the set sound speeds and an actual sound speed are different from each other, coherency between the echo signals of channels is reduced, which leads to a reduction in image quality.

Therefore, in a technique described in David Napolitano, et. al, "Sound speed correction in ultrasound imaging, Ultrasounds", Volume 44, p43-46 (2006), ISSN 0041-624X (Non-Patent Literature 1), the channel RF signals obtained from an imaging target are temporarily stored, the sound speed used for receive beamforming is changed into a plurality of types, and the delay times for the sound speeds are calculated. Receive beamforming is performed using the calculated delay times, an ultrasound image is generated for each of the plurality of types of sound speeds, and a degree of focus of each image is evaluated. An optimum delay time is determined based on the obtained degree of focus, and an ultrasound image is generated. Accordingly, the ultrasound image can be imaged at a sound speed suitable for the imaging target. The sound speed for beamforming at which such a best image is obtained is referred to as an average sound speed or the like in distinction from the sound speed as a physical property value of the tissue. When the sound speed as the physical property value of the imaging target is uniform, the average sound speed coincides with the sound speed as the physical property value, but when the imaging target has a plurality of sound speeds as the physical property value, the average sound speed in a propagation path of the ultrasound waves is estimated as an optimal sound speed for beamforming.

Meanwhile, S. M. Hverven, O. M. H. Rindal, A. Rodriguez-Molares and A. Austeng, "The influence of speckle statistics on contrast metrics in ultrasound imaging", 2017 IEEE International Ultrasounds Symposium (IUS), Washington, DC, USA, 2017, pp. 1-4 (Non-Patent Literature 2) discloses an adaptive-beamforming technique that reduces artifacts and noise components having low coherence by weighting a signal in accordance with coherence of the received signals.

SUMMARY OF THE INVENTION

Since the imaging target includes a plurality of tissues having different sound speeds in a complicated arrangement, if the degree of focus can be evaluated in units of pixels, pixels having high coherence can be extracted, robustness and accuracy of sound speed estimation can be improved, and high-quality imaging with reduced artifacts and noise can be performed.

However, the technique of Non-Patent Literature 1 can generate an ultrasound image for each of the plurality of types of sound speeds and evaluate the degree of focus of each image, but cannot evaluate the degree of focus in units of pixels.

Meanwhile, in the adaptive-beamforming technique, since correlation calculation between the echo signals of the channels is used, an amount of calculation is large, and it is necessary to mount an adaptive-beamforming dedicated circuit, dedicated software, or the like at a front end of the device.

An object of the present disclosure is to calculate a coherence indicator of received signals for pixels with a small amount of calculation and obtain a high-quality ultrasound image.

Solution to Problem

In order to achieve the above object, an ultrasound imaging device according to the present disclosure includes a memory that stores received signals, an ultrasound image generation unit, an image generation unit of different sound speed, and a coherence indicator calculation unit. The memory stores the received signals to be output from each of ultrasound probe elements, the ultrasound probe elements are arranged in a row and receive ultrasound waves reflected by an imaging target that receives transmission of the ultrasound waves. The ultrasound image generation unit receives the received signals of the plurality of ultrasound probe elements from the memory and performs receive beamforming processing using a delay time set based on a sound speed for beamforming to generate an image in a predetermined imaging range. The image generation unit of different sound speed causes the ultrasound image generation unit to generate a plurality of types of images in which the sound speed for beamforming is changed into a plurality of types, or to generate the plurality of types of images based on data of the image generated by the ultrasound image generation unit. The coherence indicator calculation unit arranges, in order of the sound speed for beamforming, signal intensities of pixels at corresponding positions between the plurality of types of images generated by the image generation unit of different sound speed to obtain a change in the signal intensities in a direction of the sound speed for beamforming, and calculates a coherence indicator representing coherence of the received signals used for beamforming of the pixels based on the obtained change in the signal intensities.

According to the present disclosure, a coherence indicator of the received signals for pixels can be calculated with a small amount of calculation, and a high-quality ultrasound image can be obtained.

BRIEF DESCRIPTION OF THE DRAWINGS

FIGS. 5A, 5B, and 5C are diagrams showing processing of an average sound speed estimation unit 56 according to the first embodiment, in which FIG. 5A is a diagram showing a distribution of coherence indicators in a ROI 71, FIG. 5B is a diagram showing a distribution of signal intensities in the ROI, and FIG. 5C is a graph showing a relation between the sound speed and a sum or an average value (a focus index) of products of the coherence indicators and the signal intensities in the ROI, which is obtained by the average sound speed estimation unit 56.

FIG. 6 is a flowchart showing operations of the ultrasound imaging device according to the first embodiment.

FIGS. 8A and 8B are diagrams showing processing of the average sound speed estimation unit 56 according to the second embodiment, in which FIG. 8A is a diagram showing a distribution of coherence indicators in the ROI 71, and FIG. 8B is a diagram showing a distribution of signal intensities in an ROI of a sound speed at which a maximum signal intensity is obtained.

FIGS. 11A, 11B, and 11C are diagrams showing processing of an image processing unit 59 according to the third embodiment, in which FIG. 11A is a diagram showing a distribution of coherence indicators in an image, FIG. 11B is a diagram showing a distribution of signal intensities in the image, and FIG. 11C is a diagram showing a distribution of signal intensities after weighting with the coherence indicators.

FIG. 12 is a flowchart showing operations of the ultrasound imaging device according to the third embodiment.

FIGS. 16A-16E are diagrams showing processing of the image generation unit of different sound speed 54 according to the fifth embodiment.

DESCRIPTION OF THE PREFERRED EMBODIMENTS

Hereinafter, embodiments of the present disclosure will be described.

In the present disclosure, ultrasound waves are transmitted to an imaging target, reflected waves or the like are received by a row of ultrasound probe elements, and a plurality of types of images on which receive beamforming is performed at a plurality of different sound speeds are generated. A coherence indicator of received signals of channels (ultrasound probe elements) used for generation of a received signal after receive beamforming constituting signal intensities of each pixel is calculated from a feature amount of a change in the signal intensities of each pixel with respect to a sound speed. Accordingly, pixels generated from a received signal having high coherence can be extracted without calculating a correlation within channel domain data (received signals of channels).

Accordingly, an optimal sound speed for beamforming (an average sound speed) corresponding to positions of pixels of an ultrasound image can be estimated. In addition, robustness and accuracy of average sound speed estimation can be improved. By performing receive beamforming processing using the estimated average sound speed, a high-quality image with reduced artifacts and noise can be imaged. Here, the optimum sound speed for beamforming is referred to as the average sound speed in distinction from a sound speed as a physical property value of a tissue. When the sound speed as the physical property value of the imaging target is uniform, the average sound speed coincides with the sound speed as the physical property value, but since the imaging target generally has a plurality of sound speeds as the physical property value, the average sound speed in a propagation path of the ultrasound waves is estimated as the optimal sound speed for beamforming. In the embodiments, the average sound speed can be estimated for each pixel of the ultrasound image.

In addition, a high-quality image can be generated by synthesizing, using coherence for each pixel, the plurality of types of images subjected to receive beamforming at different sound speeds.

First Embodiment

Figure 1:
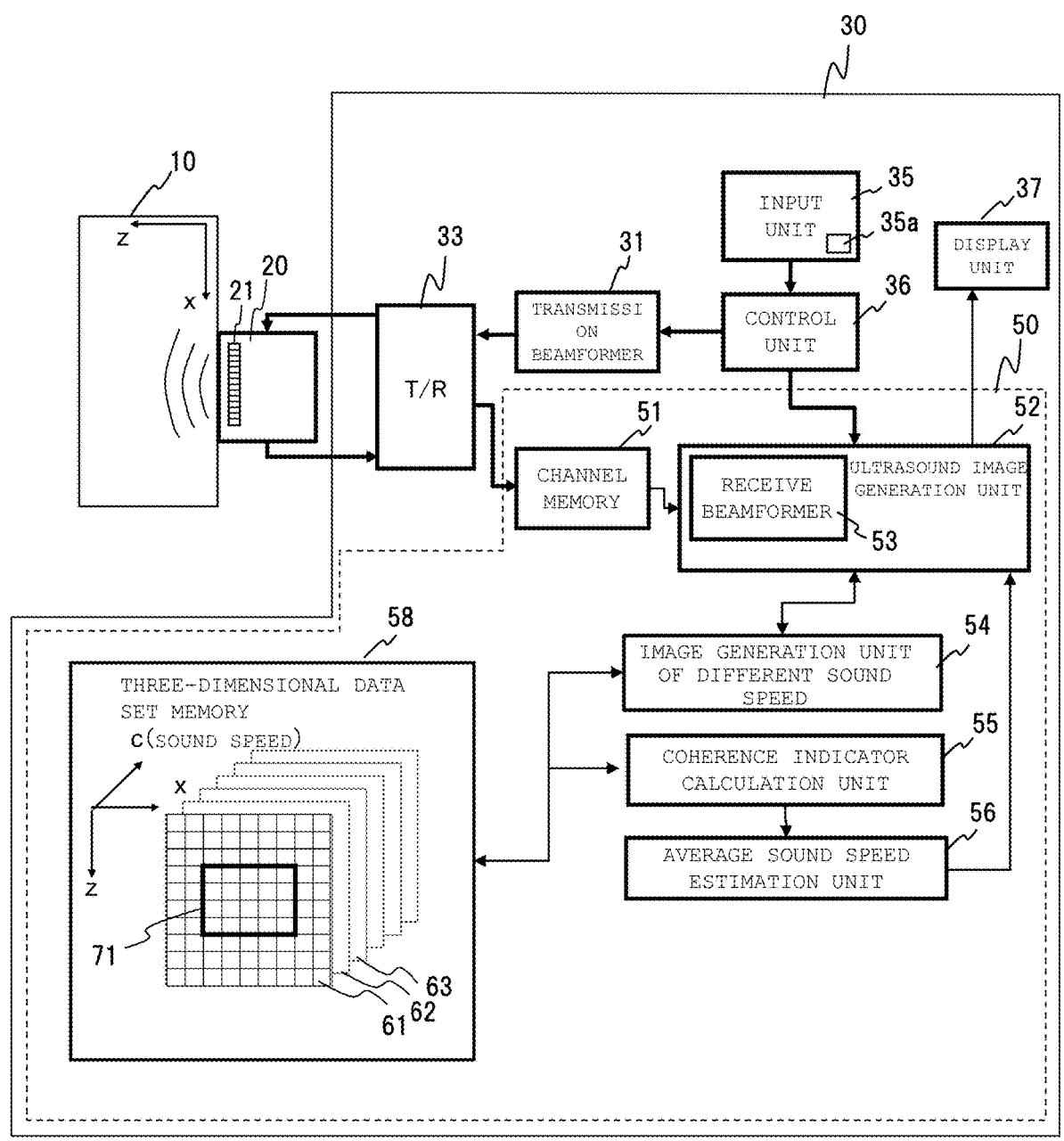
FIG. 1 is a block diagram showing a configuration of an ultrasound imaging device according to a first embodiment.

Hereinafter, an ultrasound imaging device according to a first embodiment will be described. FIG. 1 is a block diagram showing an overall configuration of the ultrasound imaging device according to the present embodiment.

In the first embodiment, after calculating coherence indicators for pixels, an average sound speed of an imaging target is estimated, and subsequent receive beamforming is performed using the estimated average sound speed.

As shown in FIG. 1, an ultrasound imaging device 30 according to the present embodiment includes a transmission beamformer 31, a transmit and receive switching unit (T/R) 33, a signal processing device 50, an input unit 35, a control unit 36, and a display unit 37. The ultrasound imaging device 30 is connected to a probe 20. A row (array) of ultrasound probe elements 21 is provided in the probe 20.

The signal processing device 50 includes, as a configuration for generating an ultrasound image, a channel memory 32 and an ultrasound image generation unit 52. In addition, the signal processing device 50 includes, as a configuration for calculating the coherence indicators, an image generation unit of different sound speed 54, a coherence indicator calculation unit 55, and a three-dimensional data set memory 58. The signal processing device 50 further includes, as a configuration for estimating the average sound speed from the coherence indicators, an average sound speed estimation unit 56.

The transmission beamformer 31 generates transmission signals and passes the transmission signals to one or more ultrasound probe elements 21 via the transmit and receive switching unit (T/R) 33. The ultrasound probe elements 21 that receive the transmission signals convert the transmission signals into ultrasound waves and transmits the ultrasound waves to an imaging target 10. The ultrasound waves reflected or the like by the imaging target 10 reach the row of ultrasound probe elements 21, and the plurality of ultrasound probe elements 21 convert the ultrasound waves into received signals (channel RF signals) and output the received signals in time series.

The time-series received signals output from the plurality of ultrasound probe elements 21 are stored in a channel memory 51.

The ultrasound image generation unit 52 includes a receive beamformer 53. The receive beamformer 53 receives the received signals of the plurality of ultrasound probe elements 21 from the channel memory 51, delays the received signals by a predetermined delay time, and then adds the received signals, thereby adjusting reception focal points to a plurality of reception focal points on predetermined scan lines (reception scan lines). The receive beamforming is sequentially performed on the plurality of reception focal points set at predetermined intervals on the scan lines, thereby obtaining received signals after receive beamforming.

The ultrasound image generation unit 52 causes the receive beamformer 53 to execute receive beamforming processing for each predetermined scan line. The ultrasound image generation unit 52 arranges the received signals after receive beamforming for each scan line that are generated by the receive beamformer 53, thereby generating an ultrasound image.

The delay time is a time obtained by dividing the distances between the reception focal points and the ultrasound probe elements 21 by a set sound speed for receive beamforming, and is generated by the ultrasound image generation unit 52 for each reception focal point of the scan line and set for the receive beamformer 53.

Figure 2A:
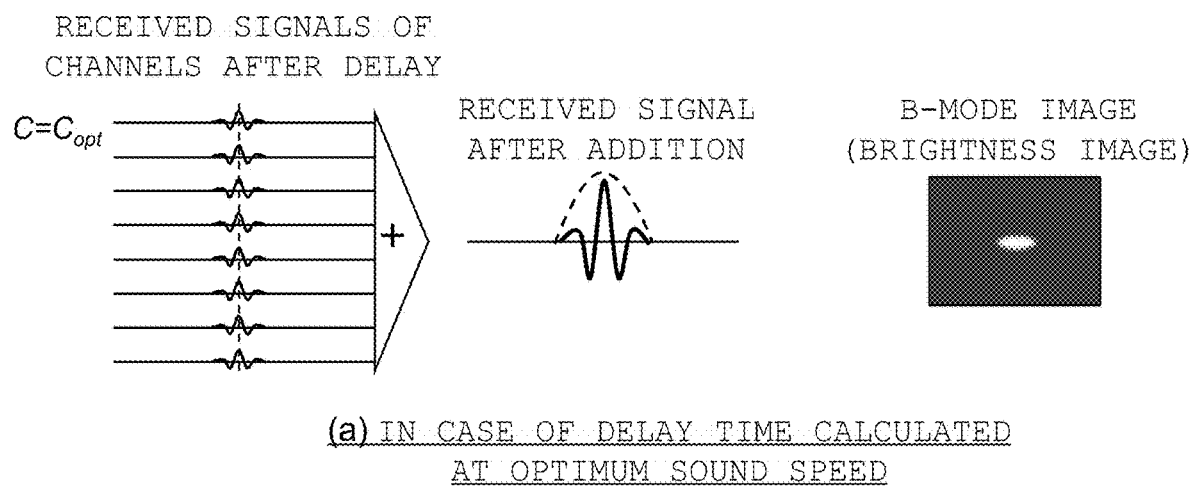
FIG. 2A is a diagram showing a waveform of a signal obtained by delaying received signals with a delay time calculated at an optimum sound speed and then adding the delayed received signals, and a B-mode image generated using the waveform.

At this time, as shown in FIG. 2A, when the sound speed for beamforming coincides with a sound speed of a tissue of an imaging target, phases of the received signals of the ultrasound probe elements 21 delayed by the receive beamformer 53 due to the delay time set based on the sound speed are matched (the coherence is high). Therefore, an amplitude of the received signals after the addition by the receive beamformer 53 increases. An ultrasound image (a B-mode image) generated using the received signals after receive beamforming has a high brightness and a small spread of the image.

Figure 2B:
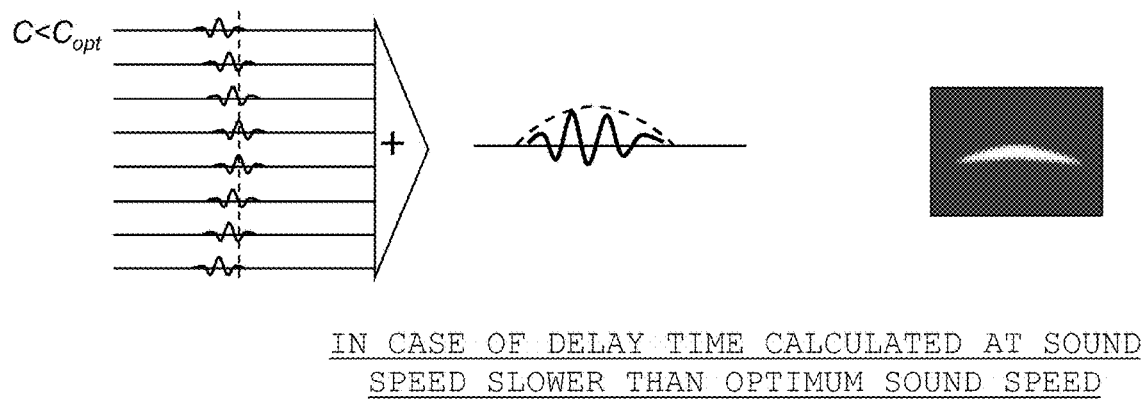
FIG. 2B is a diagram showing a waveform of a signal obtained by delaying received signals with a delay time calculated at a sound speed slower than the optimum sound speed and then adding the delayed received signals, and a B-mode image generated using the waveform.

On the other hand, as shown in FIG. 2B, when the sound speed for beamforming is slower than the sound speed of the tissue of the imaging target, the received signals of the ultrasound probe elements 21 delayed by the receive beamformer 53 due to the delay time set based on the sound speed do not have the same phase (have low coherence) as compared to the case in FIG. 2A. Therefore, the amplitude of the received signals after the addition by the receive beamformer 53 becomes smaller than that in the case in FIG. 2A, and the spread of the signals becomes larger. The ultrasound image (the B-mode image) in FIG. 2B generated using the received signals after receive beamforming has a lower brightness and a larger spread of the image as compared to FIG. 2A.

In the present embodiment, attention is paid to the fact that brightness of a pixel varies depending on the sound speed for beamforming as shown in FIGS. 2A and 2B, and the coherence after delay of received signals used to generate the pixel is evaluated.

First, the image generation unit of different sound speed 54 causes the ultrasound image generation unit 52 to generate a plurality of types of images in which the sound speed for beamforming is changed into a plurality of types. Specifically, the image generation unit of different sound speed 54 causes the ultrasound image generation unit 52 to sequentially set the sound speeds for beamforming in a predetermined range and interval (for example, sound speeds obtained by selecting a sound speed in a range of 1400 to 1650 m/s at an interval of 10 m/s) and to sequentially generate images for the sound speeds for beamforming. The ultrasound image generation unit 52 calculates a delay time for each set sound speed for beamforming, and sets the delay time for the receive beamformer 53. Accordingly, the ultrasound image generation unit 52 sequentially generates a plurality of types of images 61, 62, 63, and so on having different sound speeds for beamforming.

Here, as shown in FIG. 1, the images 61, 62, 63, and so on are images on a two-dimensional plane in a direction of the row (x direction) of the ultrasound probe elements 21 and a depth direction (z direction) of the imaging target 10. The image generation unit of different sound speed 54 arranges the plurality of types of images 61, 62, 63, and so on in a direction of the sound speed (c direction) for beamforming, generates a three-dimensional data set, and stores the generated images in the three-dimensional data set memory 58.

Figure 3A:
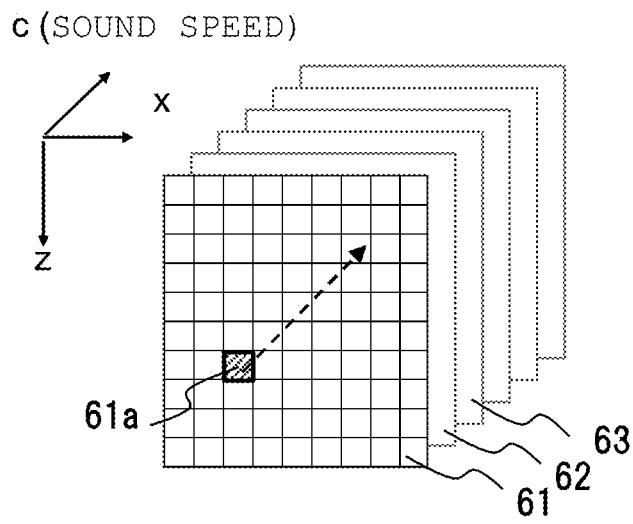
FIGS. 3A and 3B are diagrams showing a three-dimensional data set generated by an image generation unit of different sound speed 54 according to the first embodiment and processing of a coherence indicator calculation unit 55.
Figure 3B:
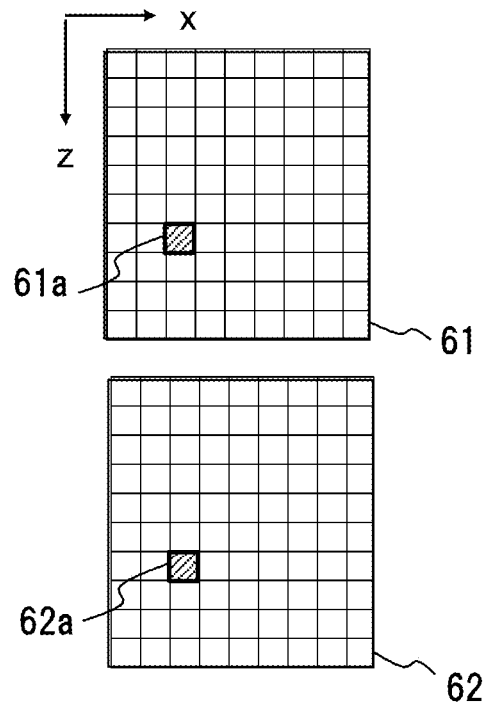
Figure 3C:
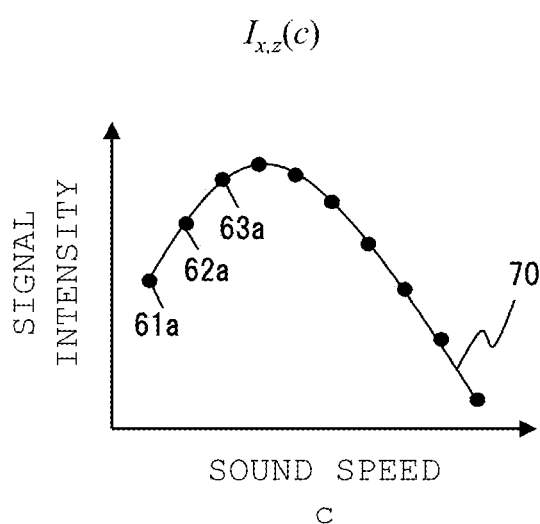
FIG. 3C is a graph showing a change, depending on a sound speed c, in brightness of corresponding pixels extracted by the coherence indicator calculation unit 55.

As shown in FIGS. 3A to 3C, the coherence indicator calculation unit 55 arranges, in the order of the sound speed c for beamforming, signal intensities of pixels 61a, 62a, and 63a at corresponding positions (for example, coordinates (x, z)=(3, 7)) of the plurality of types of images 61, 62, 63, and so on. Specifically, as the signal intensity, an amplitude value after detection may be used, or an amplitude value after log compression may be used. Accordingly, a change in the signal intensities in the direction of the sound speed (c direction) for beamforming is obtained, and a coherence indicator representing the coherence of a plurality of received signals used for receive beamforming of the pixels 61a, 62a, and 63a is calculated based on the obtained change in the signal intensities.

Specifically, as shown in FIG. 3C, the coherence indicator calculation unit 55 generates a graph representing the change in the signal intensities of the corresponding pixels 61a, 62a, 63a, and so on of the plurality of types of images 61, 62, 63, and so on having different sound speeds for beamforming, with the sound speed c for beamforming as the horizontal axis and the magnitude of the signal intensity as the vertical axis. In the graph, the coherence indicator calculation unit 55 obtains a curve 70 representing the change in the signal intensities.

Figure 4A:
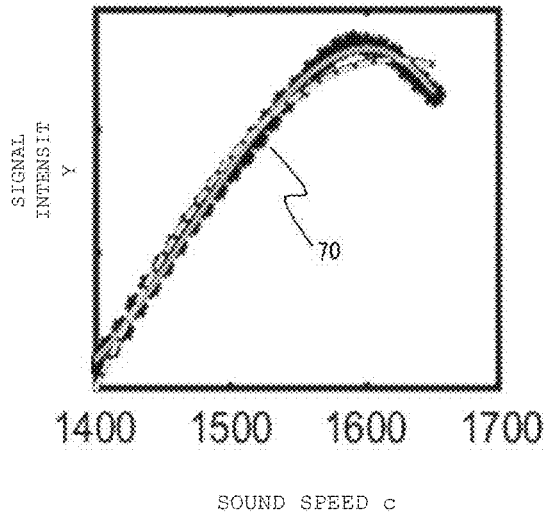
FIG. 4A is a graph showing a relation between the brightness and the sound speed of a pixel having high coherence according to the first embodiment.

As shown in FIG. 4A, the inventors have found that, in a case where the pixels 61a, 62a, 63a, and the like are pixels obtained by imaging an actual signal having high coherence, such as a structure in the imaging target 10, the curve 70 has the maximum amplitude at the optimum sound speed (the sound speed of the tissue at the pixel position of the imaging target 10), a convex upward shape (mountain shape), and can be relatively well approximated by a quadratic polynomial. That is, when the curve 70 is approximated by the quadratic polynomial, a quadratic coefficient is a negative value, and a determination coefficient $R^2$ in a multiple regression analysis is high. The determination coefficient $R^2$ is calculated by Formula (1).

$$R^2 = 1 - \frac{\sum_{i=1}^{N}(a_i - b_i)^2}{\sum_{i=1}^{N}(a_i - \bar{a})^2} \quad (1)$$

where $a_i$: signal intensity at an i-th candidate sound speed, and $b_i$: signal intensity at an i-th candidate sound speed in polynomial approximation of $a_i$.

Figure 4B:
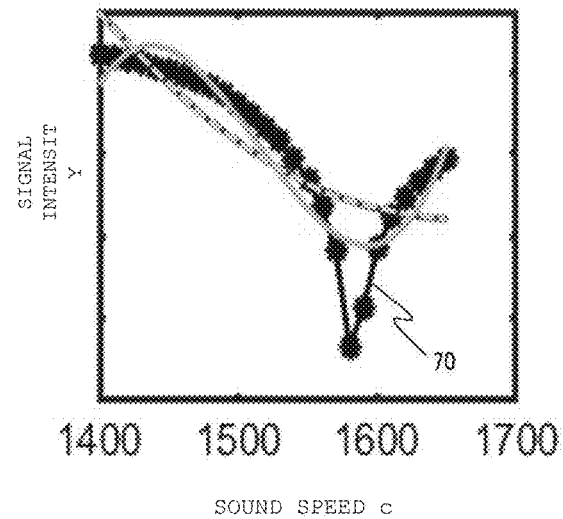
FIG. 4B is a graph showing a relation between the brightness and the sound speed of a pixel having low coherence according to the first embodiment.

On the other hand, as shown in FIG. 4B, in a case where the pixels 61a, 62a, 63a, and the like are pixels obtained by imaging a signal having low coherence such as an artifact component such as a side lobe or a noise component, the amplitude is low at the optimum sound speed (the sound speed of the tissue at the pixel position of the imaging target 10), the shape is convex downward (valley shape), and a complicated change pattern such as having a constriction is seen. Therefore, the curve 70 cannot be approximated well by a quadratic polynomial. That is, when the curve 70 is approximated by a quadratic polynomial, the quadratic coefficient is a positive value, and the determination coefficient $R^2$ in the multiple regression analysis is low.

Therefore, the coherence indicator calculation unit 55 calculates at least one feature amount among whether the curve 70 has an upward convex shape, an amount of change in the curve, an approximation accuracy of the curve to a predetermined polynomial, and an extreme value of the curve, and calculates the coherence indicator from one or more feature amounts.

As an example, the coherence indicator calculation unit 55 calculates the coherence indicator by the following Formula (2) and Formula (3). In Formula (2), a variable h is used, and when the quadratic coefficient in the quadratic polynomial approximation is equal to or greater than 0, the variable h is set to 0, and when the quadratic coefficient in the quadratic polynomial approximation is negative, that is, when the curve has an upward convex shape (mountain shape), the determination coefficient $R^2$ calculated by Formula (1) in the quadratic polynomial approximation is set to the value of the variable h. Then, using the variable h, a coherence indicator $W_{CF}$ is calculated using a weighting function in which the output increases from 0 to 1 as the variable h increases from 0 to 1, as shown in Formula (3).

$$h=0 (p_2 \geq 0)$$

$$h=R^2 (p_2 < 0) \quad (2)$$

where p2: quadratic coefficient in quadratic polynomial approximation.

$$W_{CF}=(\sin((h-0.5)*\pi)+1)/2 \quad (3)$$

The average sound speed estimation unit 56 estimates an average sound speed of the imaging target 10 corresponding to the positions of the pixels 61a, 62a, 63a, that is, the optimum sound speed for beamforming, using the coherence indicator calculated by the coherence indicator calculation unit 55 and the signal intensities of the pixels 61a, 62a, 63a, and so on of the plurality of types of images 61, 62, 63, and the like having different sound speeds c for beamforming.

A method for estimating the average sound speed will be described.

As shown in FIG. 1, the coherence indicator calculation unit 55 calculates the coherence indicators for a plurality of pixels included in the predetermined ROI 71 within an imaging range (a range of images 61, 62, and 63) of the imaging target 10. Accordingly, for example, as shown in FIG. 5A, a distribution of the coherence indicators in the ROI 71 is obtained.

The average sound speed estimation unit 56 calculates, for each pixel 61a and the like in the ROI 71 of one image 61, a product of the signal intensity and the coherence indicator of the pixel, and calculates a sum or an average value of the calculated products in the ROI 71. The sum or the average value is referred to as a focus indicator. The average sound speed estimation unit 56 also calculates the focus indicator for each of the corresponding ROIs 71 of the other images 62 and 63 and the like having different sound speeds c for beamforming.

The average sound speed estimation unit 56 plots the obtained focus indicators and the sound speeds c for beamforming of the obtained image as shown in FIG. 5C, and estimates the sound speed c for beamforming having a maximum focus index as the average sound speed of the region of the imaging target 10 corresponding to the ROI 71.

The average sound speed estimation unit 56 sets the estimated average sound speed as the sound speed c for beamforming for the ultrasound image generation unit 52. Accordingly, the average sound speed estimation unit 56 causes receive beamforming of subsequent imaging by the ultrasound image generation unit 52 to be executed using the sound speed c for beamforming that coincides with the average sound speed of the ROI 71.

Hereinafter, operations of units of the ultrasound imaging device including the signal processing device 50 according to the present embodiment will be described based on a flowchart in FIG. 6.

The signal processing device 50 is configured with a computer or the like including a processor such as a central processing unit (CPU) or a graphics processing unit (GPU) and a memory, and the CPU reads and executes a program stored in the memory to implement functions of the units 52 to 56 of the signal processing device 50 by software. In addition, a part or all of the signal processing device 50 may also be implemented by hardware. For example, the signal processing device 50 may be configured using a custom IC such as an application specific integrated circuit (ASIC) or a programmable IC such as a field-programmable gate array (FPGA), and circuit design may be performed to implement the functions of the units of the signal processing device 50.

First, a user instructs imaging via the input unit 35, calculates the coherence indicator, estimates the average sound speed, and presses a button 35a when the estimated average sound speed is set for the receive beamformer 53. When the button 35a is pressed, the control unit 36 causes the units to execute the flow in FIG. 6.

Step 201

First, the transmission beamformer 31 causes the ultrasound waves to be transmitted from the ultrasound probe elements 21 toward the imaging target 10. The ultrasound waves reflected or the like by the imaging target 10 are converted into the received signals (channel RF signals) by the row of the ultrasound probe elements 21. The received signals from the plurality of ultrasound probe elements 21 are stored in the channel memory 51.

Step 202

The receive beamformer 53 reads the received signals (channel RF signals) of the ultrasound probe elements 21 from the channel memory 51, and performs phasing addition by a known receive beamforming method such as a delay and sum method or a Fourier phasing method using a delay time calculated from the sound speed c set in advance. Accordingly, a signal after beamforming is obtained for each of the plurality of reception focal points along one or more scan lines set in the imaging range.

Step 203

The receive beamformer 53 repeats the above step 202 until all the signals after beamforming necessary for generating an image of one frame are obtained.

Step 204

The ultrasound image generation unit 52 arranges the signals after beamforming of the scan line for one frame and generates an image. The image generation unit of different sound speed 54 receives the generated image and stores the image in the three-dimensional data set memory 58.

Step 205

The image generation unit of different sound speed 54 changes the sound speed c for receive beamforming and sets the changed sound speed c for the ultrasound image generation unit 52. The ultrasound image generation unit 52 calculates a delay time using the changed sound speed c for receive beamforming, and sets the delay time for the receive beamformer 53.

Step 206

The receive beamformer 53 repeats steps 202 to 204 using the changed sound speed c for receive beamforming, thereby generating an image using the changed sound speed c for receive beamforming. The image generation unit of different sound speed 54 receives the generated image and stores the image in the three-dimensional data set memory 58. Step 206 is repeated until all types of sound speeds c for receive beamforming are set. Accordingly, the ultrasound image generation unit 52 generates the plurality of types of images 61, 62, 63, and so on having different sound speeds c for receive beamforming.

The image generation unit of different sound speed 54 receives the generated plurality of types of images 61, 62, 63, and so on from the ultrasound image generation unit 52, arranges the images in the direction of the sound speed (c direction) for receive beamforming, generates a three-dimensional data set, and stores the generated images in the three-dimensional data set memory 58.

Step 207

The coherence indicator calculation unit 55 generates the curve 70 representing the change in the signal intensities of the pixels 61a, 62a, and 63a arranged in the direction of the sound speed of the three-dimensional data set in the ROI 71 as shown in FIG. 3C, and calculates the coherence indicator using Formula (1).

Step 208

The average sound speed estimation unit 56 calculates, for each of the images 61, 62, 63, and the like, the sum or the average value of the products of the signal intensities and the coherence indicators of the pixel 61a in the ROI 71 as the focus index.

Step 209

The average sound speed estimation unit 56 estimates that the sound speed c for beamforming having the maximum focus indicator is the average sound speed of the region of the imaging target 10 corresponding to the ROI 71. The average sound speed estimation unit 56 sets the estimated average sound speed as the sound speed c for beamforming for the ultrasound image generation unit 52.

By the above steps 201 to 209, the sound speed c for beamforming that coincides with the average sound speed of the ROI 71 is set for the ultrasound image generation unit 52. The ultrasound imaging device can perform subsequent imaging at an optimal sound speed. Accordingly, it is possible to image a high-quality image with reduced artifacts and noise.

In the present embodiment, as shown in FIG. 6, a configuration in which the sound speed c for receive beamforming is changed and images are generated one by one has been described, but the present disclosure is not limited to this configuration. In a case where the ultrasound image generation unit 52 includes a plurality of receive beamformers 53, the image generation unit of different sound speed 54 may set delay times of a plurality of types of sound speeds c for beamforming for the plurality of receive beamformers 53, respectively, and cause the plurality of receive beamformers 53 to perform beamforming processing in parallel on the same scan line. Accordingly, it is possible to generate, in parallel, a plurality of types of images having different sound speeds c for receive beamforming.

Second Embodiment

Figure 7:
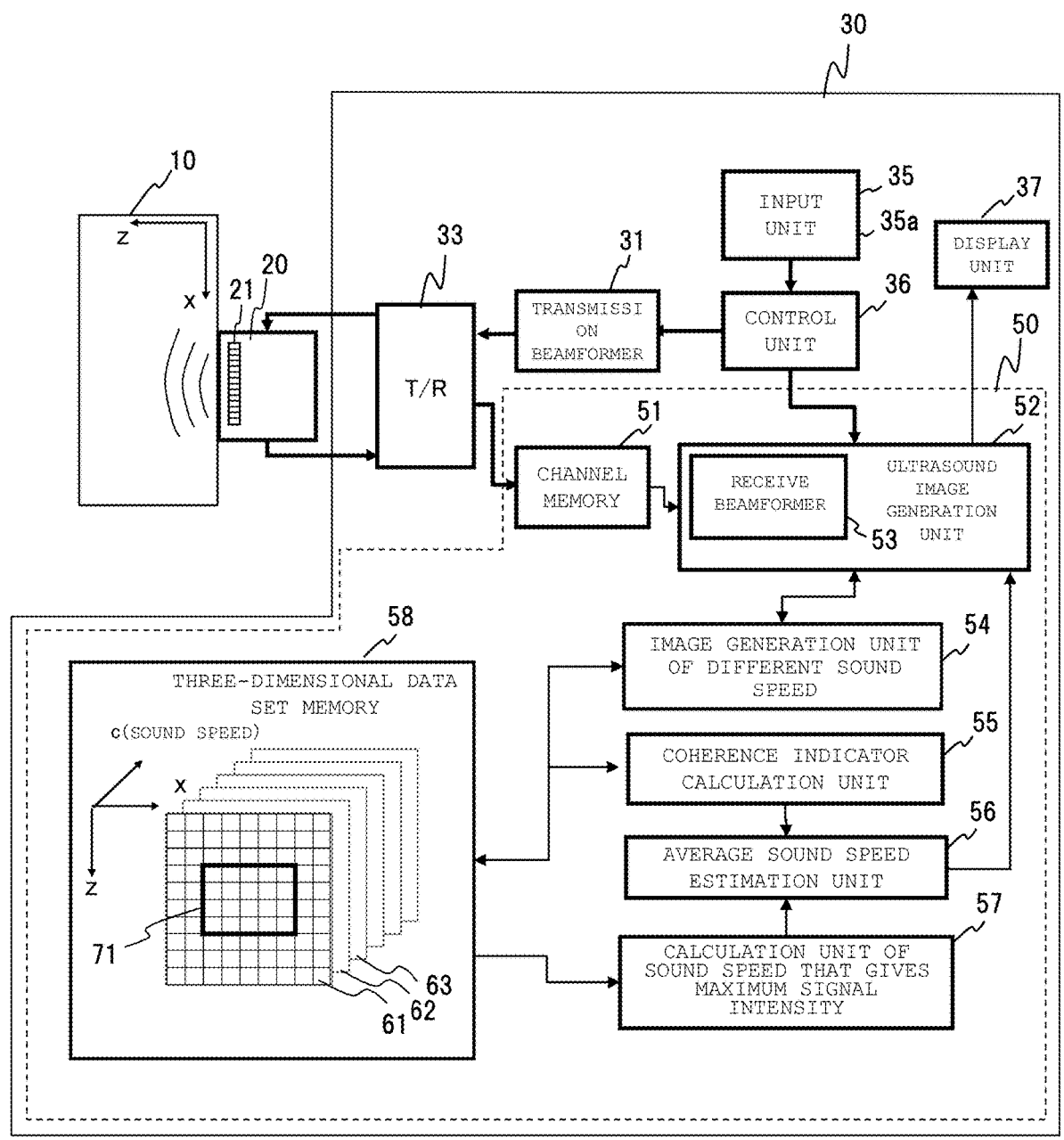
FIG. 7 is a block diagram showing a configuration of an ultrasound imaging device according to a second embodiment.
Figure 9:
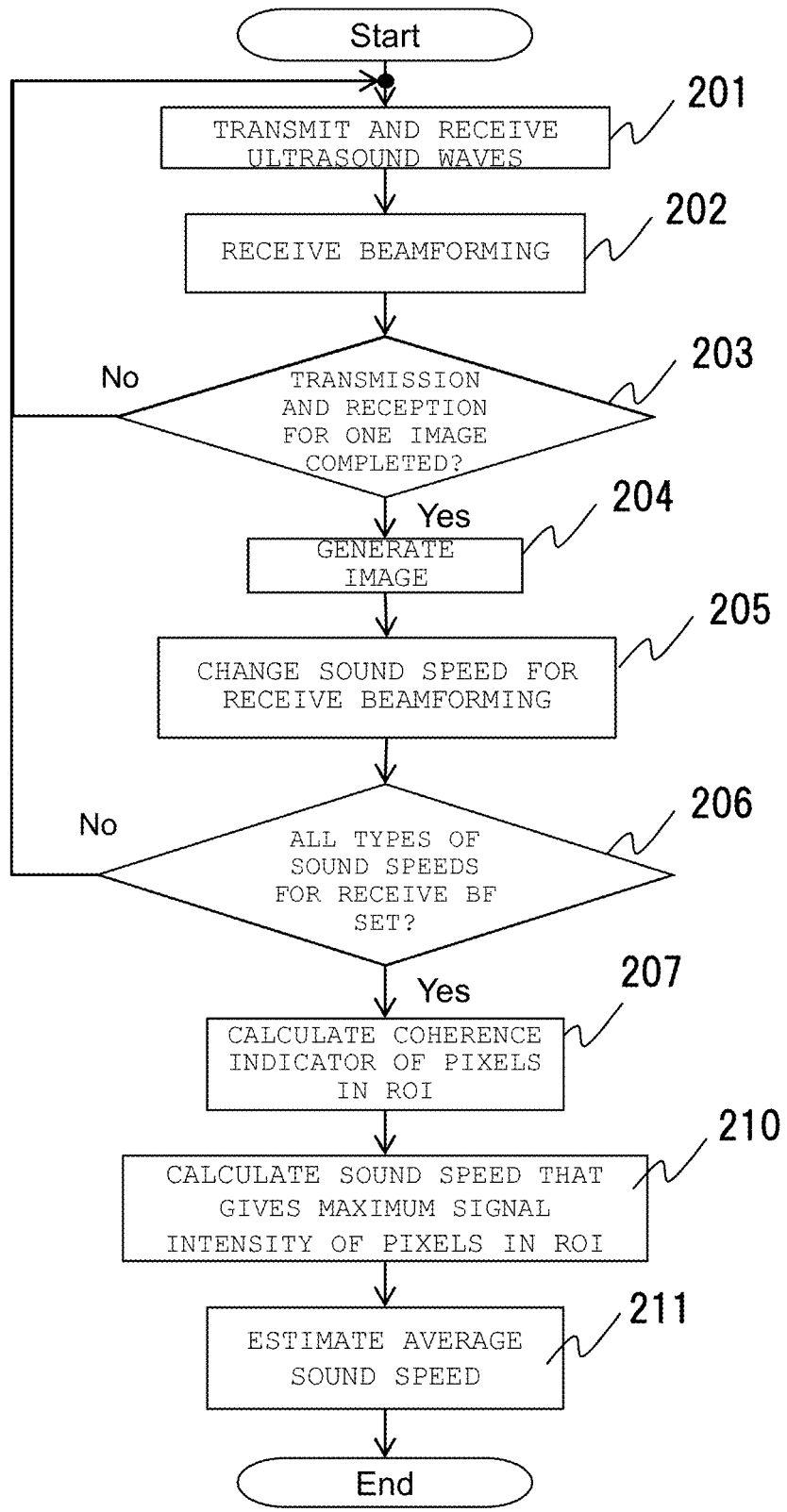
FIG. 9 is a flowchart showing operations of the ultrasound imaging device according to the second embodiment.

An ultrasound imaging device according to a second embodiment will be described. FIG. 7 is a block diagram showing an overall configuration of the ultrasound imaging device according to the present embodiment. FIG. 8 is a diagram showing processing of the average sound speed estimation unit 56 according to the present embodiment. FIG. 9 is a flowchart showing operations of the ultrasound imaging device according to the present embodiment.

The ultrasound imaging device according to the second embodiment has the same configuration and operations as those of the ultrasound imaging device according to the first embodiment, but differs from the ultrasound imaging device according to the first embodiment in that a calculation unit of the sound speed that gives the maximum signal intensity 57 is further provided as shown in FIG. 7, and in the processing when the average sound speed estimation unit 56 estimates the average sound speed which is the optimal sound speed for beamforming of an imaging target. Hereinafter, the differences will be mainly described.

As shown in FIG. 9, the processing of the ultrasound imaging device according to the second embodiment is the same as the flow in FIG. 6 according to the first embodiment from steps 201 to 207. Accordingly, in step 207, the coherence indicator calculation unit 55 calculates coherence indicators for pixels in the ROI 71. Accordingly, as shown in FIG. 8A, a distribution of the coherence indicators in the ROI 71 is obtained.

Step 210

In step 210, the calculation unit of the sound speed that gives the maximum signal intensity 57 compares the signal intensities of the pixels (for example, the pixel 61a of the image 61) in the ROIs 71 corresponding to the plurality of types of images 61, 62, 63, and so on having different sound speeds for beamforming with the signal intensities of the pixels 62a, 63a, and so on at the corresponding positions of the other images 62, 63, and so on. Accordingly, an image having a maximum signal intensity is selected from the images 61, 62, 63, and so on. The sound speed c for beamforming used at the time of generating the selected image is set as the sound speed that gives the maximum signal intensity at the position of the pixel 61a.

By performing step 210 for each pixel in the ROI 71, the calculation unit of the sound speed that gives the maximum signal intensity 57 obtains the distribution of sound speeds that give the maximum signal intensity in the ROI 71 as shown in FIG. 5B.

Step 211

The average sound speed estimation unit 56 estimates, for each pixel, the average sound speed using a weighted sound speed that gives the maximum signal intensity obtained by weighting the sound speed that gives the maximum signal intensity using the coherence indicator. Specifically, for example, as shown in FIG. 8, the average sound speed estimation unit 56 obtains the weighted sound speed that gives the maximum signal intensity for each pixel in the ROI 71, and sets the average value as the average sound speed.

Accordingly, the average sound speed estimation unit 56 sets the estimated average sound speed as the sound speed c for beamforming for the ultrasound image generation unit 52.

By the above steps 201 to 207, 210, and 211, the sound speed c for beamforming that coincides with the average sound speed of the ROI 71 is set for the ultrasound image generation unit 52, and therefore the ultrasound imaging device can perform subsequent imaging at an optimal sound speed. Accordingly, it is possible to image a high-quality image with reduced artifacts and noise.

In the second embodiment, the coherence indicator and the sound speed that gives the maximum signal intensity signal intensity are obtained for all the pixels in the ROI 71 in steps 207 and 210, but the coherence indicator and the sound speed that gives the maximum signal intensity may not necessarily be obtained for all the pixels. The coherence indicator and the sound speed that gives the maximum signal intensity may be obtained for only some pixels, the weighted sound speed that gives the maximum signal intensity may be calculated, and the average value thereof may be set as the average sound speed.

In addition, the distribution of the coherence indicator and the distribution of the sound speeds that give the maximum signal intensity in the ROI may be calculated by interpolation calculation or the like after obtaining the coherence indicator and the sound speed that gives the maximum signal intensity for only some pixels in the ROI. Further, the distribution of the sound speeds that give the maximum signal intensity in the ROI may be weighted by the distribution of the coherence indicators, the distribution of the weighted sound speeds that gives the maximum signal intensity may be obtained, and the average value of the distribution of the weighted sound speeds that gives the maximum signal intensity may be set as the average sound speed.

Third Embodiment

Figure 10:
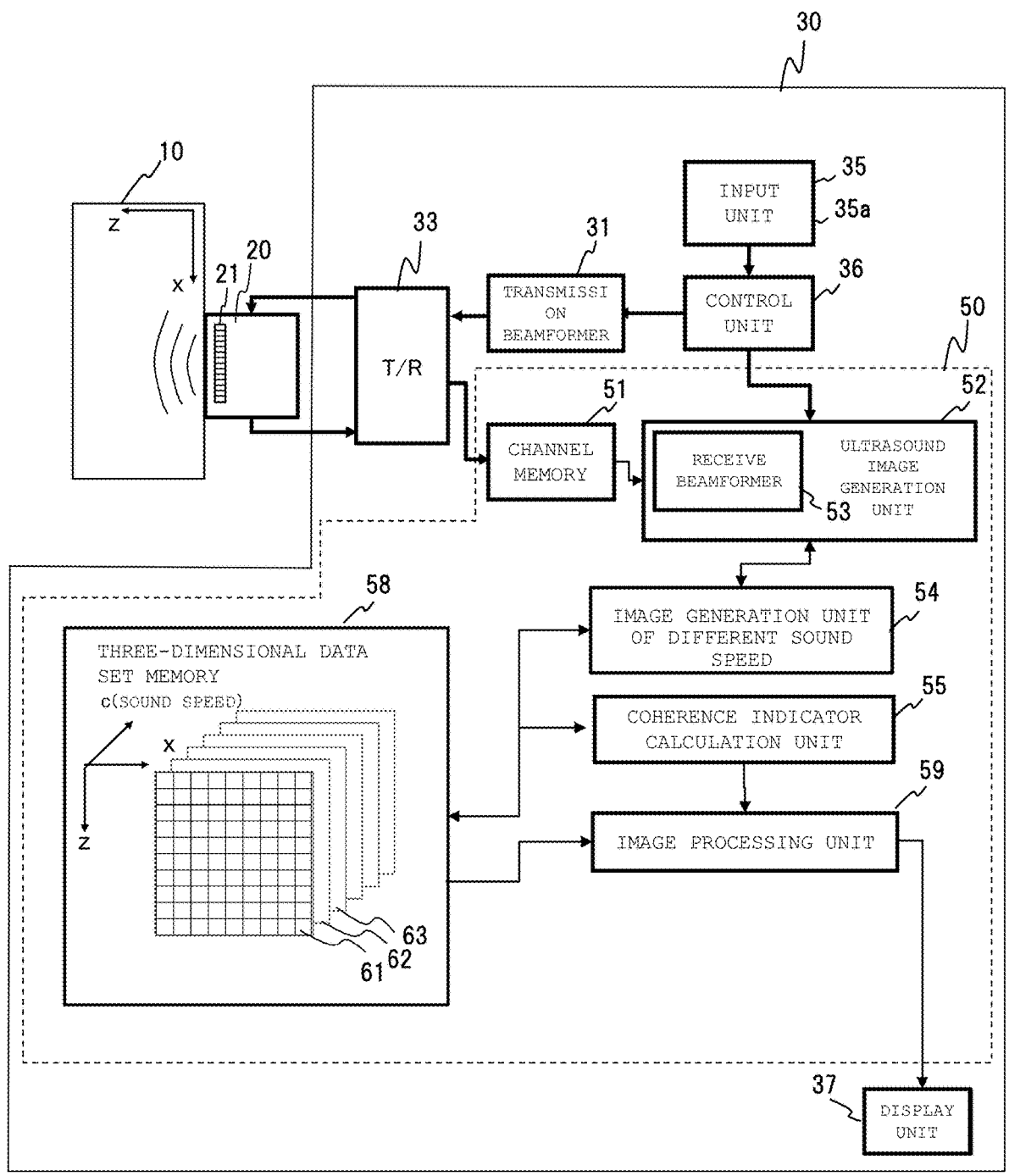
FIG. 10 is a block diagram showing a configuration of an ultrasound imaging device according to a third embodiment.
Figure 11:
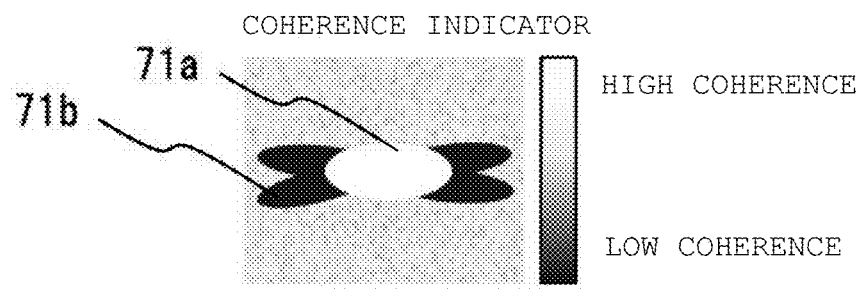
Figure 11:
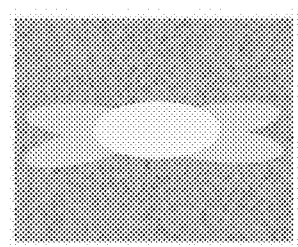

An ultrasound imaging device according to a third embodiment will be described. FIG. 10 is a block diagram showing an overall configuration of the ultrasound imaging device according to the present embodiment. FIG. 11 is a diagram showing processing of an image processing unit 59 according to the present embodiment. FIG. 12 is a flowchart showing operations of the ultrasound imaging device according to the present embodiment.

In the third embodiment, a high-quality image with reduced noise and artifacts is generated by weighting an image using coherence for each pixel.

The ultrasound imaging device according to the third embodiment has the same configuration and operations as those of the ultrasound imaging device according to the first embodiment, but is different from the first embodiment in that instead of the average sound speed estimation unit 56, the image processing unit 59 is provided as shown in FIG. 10. Hereinafter, the differences will be mainly described.

As shown in FIG. 12, the processing of the ultrasound imaging device according to the third embodiment is the same as the flow in FIG. 6 according to the first embodiment from steps 201 to 207. Accordingly, in step 207, the coherence indicator calculation unit 55 calculates coherence indicators for pixels in the image, respectively. In the second embodiment, the coherence indicator calculation unit 55 calculates coherence indicators for pixels in the ROI 71, respectively, to obtain the distribution of the coherence indicators in the ROI, but in the third embodiment, the coherence indicator calculation unit 55 calculates the coherence indicators for the pixels in the entire image, respectively. Accordingly, as shown in FIG. 11A, the distribution of the coherence indicators in the image is obtained.

Steps 212 and 213

Figure 11C:
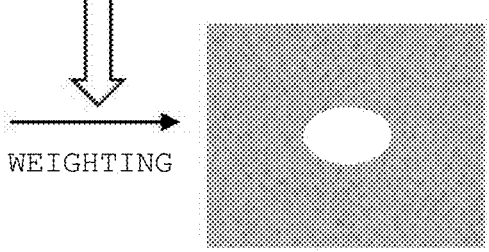

In step 212, the image processing unit 59 generates a processed image using the signal intensities of one or more images among the plurality of types of images 61, 62, 63, and so on having different sound speeds for beamforming (FIG. 11B) and the distribution of the coherence indicators of the entire image obtained in step 207. Specifically, the image processing unit 59 generates an image by weighting one image of the plurality of types of images 61, 62, 63, and so on such that the signal intensity of a first region 71a having a high coherence indicator in the image is larger than the signal intensity of a second region 71b having lower coherence than that of the first region 71a (FIG. 11C). The generated image is displayed on the display unit 37.

According to the present embodiment, as shown in FIG. 11C, it is possible to prevent a signal having low coherence and, conversely, to enhance a signal having high coherence, and to reduce the signal intensity caused by artifacts such as side lobes and grating lobes. Accordingly, it is possible to generate a high-quality image in which the visibility of an actual signal of a structure in the imaging target 10 is improved.

As one image to be subjected to image processing by the image processing unit 59, an image having a general specified sound speed such as 1540 m/s among the plurality of types of images 61, 62, 63, and so on can be used. Alternatively, an image having an average sound speed estimated in a predetermined ROI 71 can be used by the method according to the first embodiment or the second embodiment.

Fourth Embodiment

Figure 13:
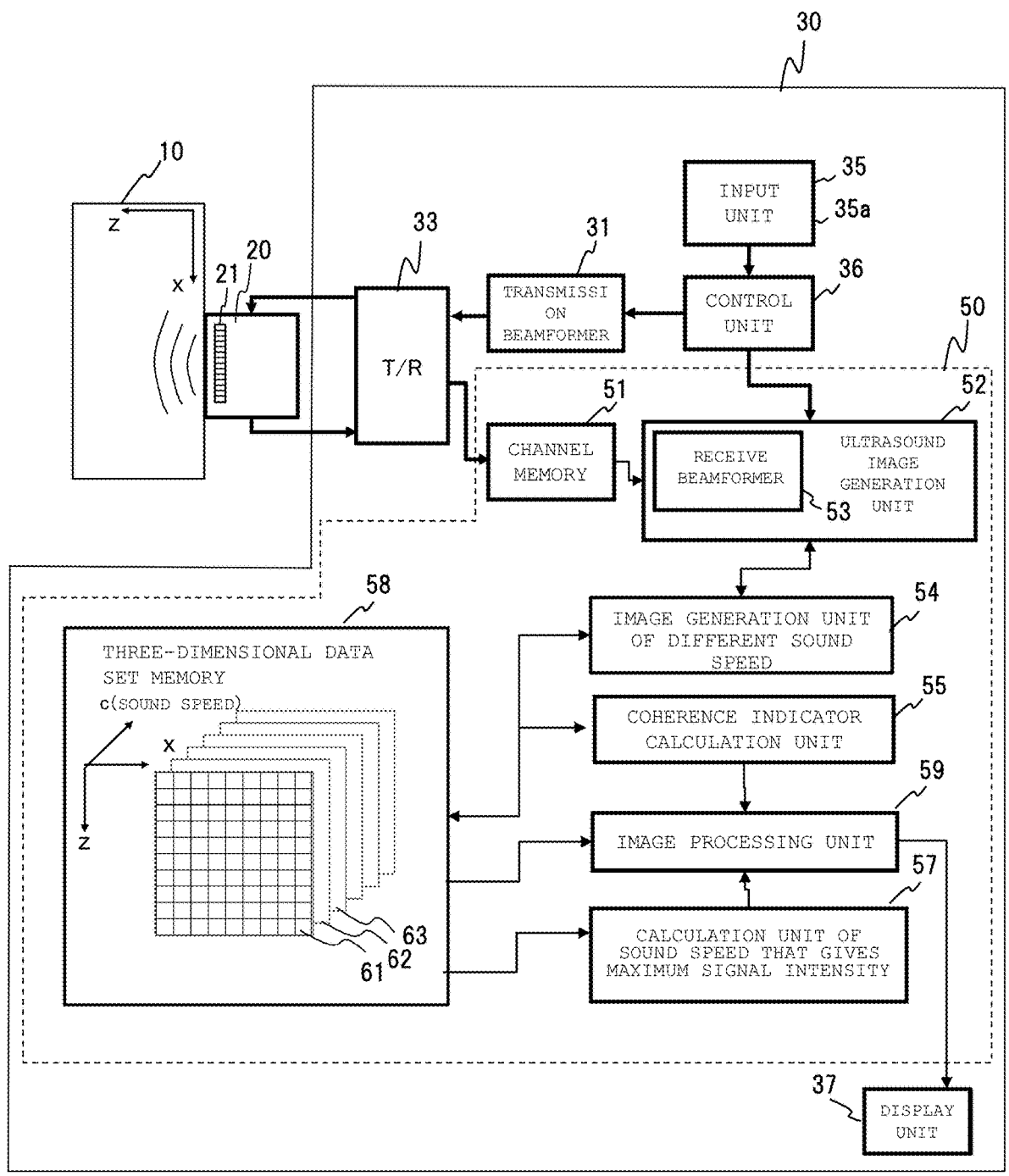
FIG. 13 is a block diagram showing a configuration of an ultrasound imaging device according to a fourth embodiment.
Figure 14:
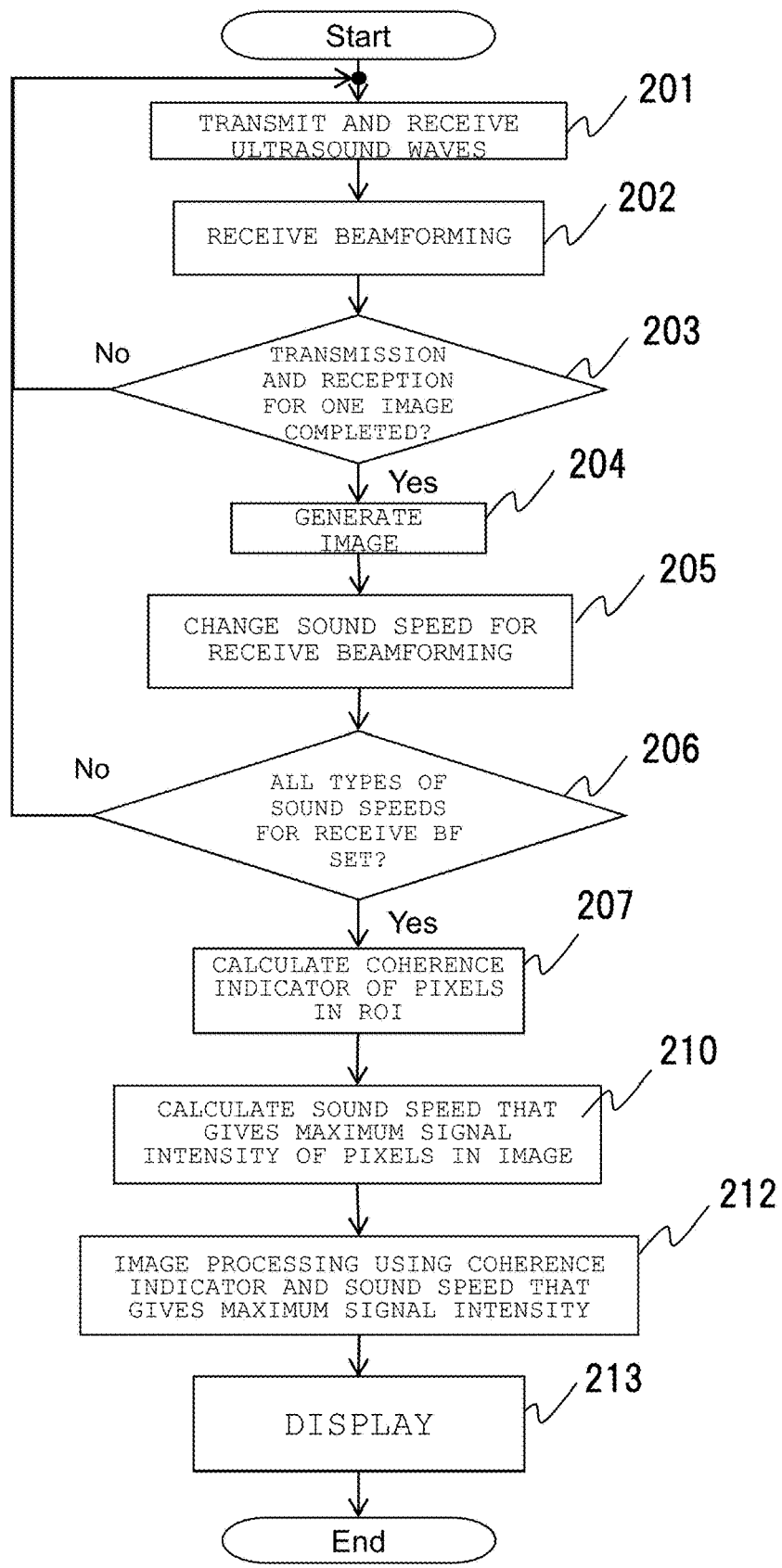
FIG. 14 is a flowchart showing operations of the ultrasound imaging device according to the fourth embodiment.

An ultrasound imaging device according to a fourth embodiment will be described. FIG. 13 is a block diagram showing an overall configuration of the ultrasound imaging device according to the present embodiment. FIG. 14 is a flowchart showing operations of the ultrasound imaging device according to the present embodiment.

In the fourth embodiment, a plurality of images are weighted using coherence of pixels and then added, thereby generating a high-quality image with reduced noise and artifacts.

The ultrasound imaging device according to the fourth embodiment has the same configuration and operations as those of the ultrasound imaging device according to the third embodiment, but is different from the ultrasound imaging device according to the third embodiment in that the calculation unit of the sound speed that gives the maximum signal intensity 57 described in the second embodiment is further provided. Hereinafter, the differences will be mainly described.

As shown in FIG. 14, the processing of the ultrasound imaging device according to the fourth embodiment is the same as the flow in FIG. 6 according to the first embodiment from steps 201 to 207. Accordingly, in step 207, the coherence indicator calculation unit 55 calculates coherence indicators for pixels in the image, respectively. Accordingly, a distribution of the coherence indicators is obtained.

Step 210

In step 210, the calculation unit of the sound speed that gives the maximum signal intensity 57 compares signal intensities of the corresponding pixels (for example, the pixel 61*a* of the image 61) of the plurality of types of images 61, 62, 63, and so on having different sound speeds for beamforming with signal intensities of the pixels 62*a*, 63*a*, and so on at corresponding positions of the other images 62, 63, and so on. Accordingly, an image having a maximum signal intensity is selected from the images 61, 62, 63, and so on. The sound speed c for beamforming used at the time of generating the selected image is set as the sound speed that gives the maximum signal intensity at the position of the pixel 61*a*.

By performing step 210 for each pixel of the image, the calculation unit of the sound speed that gives the maximum signal intensity 57 obtains a distribution of the sound speeds that give the maximum signal intensities.

Step 212

The image processing unit 59 performs weighted addition on the signal intensities of the pixels 61*a*, 62*a*, 63*a*, and so on at corresponding positions of the plurality of types of images 61, 62, 63, and so on having different sound speeds for beamforming. At this time, the image processing unit 59 sets a weight of the signal intensity of the image in which the sound speed that gives the maximum signal intensity is set as the sound speed for beamforming at the time of weighting such that the weight of the signal intensity of the image increases as the coherence indicator increases. Accordingly, it is possible to set the weight of the pixel having the sound speed that gives the maximum signal intensity to be large, to set the weight of the pixel having the large coherence indicator among the pixels to be large, and to add the signal intensities of the corresponding pixels 61*a*, 62*a*, 63*a*, and so on of the plurality of images 61, 62, 63, and so on.

Accordingly, since the signal intensities of the plurality of images can be added, robustness is improved as compared with a case where one image is processed. In addition, it is possible to prevent a signal having low coherence and, conversely, to enhance a signal having high coherence, to reduce the signal intensity caused by artifacts such as side lobes and grating lobes, and to generate a high-quality image in which the visibility of an actual signal of a structure in the imaging target 10 is improved.

In the fourth embodiment, in addition to the calculation unit of the sound speed that gives the maximum signal intensity 57, a minimum signal intensity acquisition sound speed calculation unit may be further provided.

The minimum signal intensity acquisition sound speed calculation unit compares the signal intensities of the pixels 61*a*, 62*a*, 63*a*, and so on at corresponding positions of the plurality of types of images 61, 62, 63, and so on having different sound speeds for beamforming with the signal intensities of one another among the plurality of types of images 61, 62, 63, and so on, and selects an image having a minimum signal intensity. The minimum signal intensity acquisition sound speed calculation unit obtains the sound speed for beamforming of the selected image as a minimum signal intensity acquisition sound speed at the position of the pixel.

In this case, at the time of weighting, the image processing unit 59 sets the weight for the pixel having the coherence value larger than a predetermined value such that the weight of the signal intensity of the image in which the sound speed that gives the maximum signal intensity is set as the sound speed for beamforming is larger than the weight of the signal intensity of the image in which the minimum signal intensity acquisition sound speed is set as the sound speed for beamforming. In addition, the image processing unit 59 sets the weight for the pixel having the coherence value smaller than the predetermined value such that the weight of the signal intensity of the image in which the minimum signal intensity acquisition sound speed is set as the sound speed for beamforming is larger than the weight of the signal intensity of the image in which the sound speed that gives the maximum signal intensity is set as the sound speed for beamforming.

Accordingly, by further using the minimum signal intensity acquisition sound speed for weighting, it is possible to set weighting more accurately than in a case of using only the minimum signal intensity acquisition sound speed, and to reduce noise and the like.

Fifth Embodiment

Figure 15:
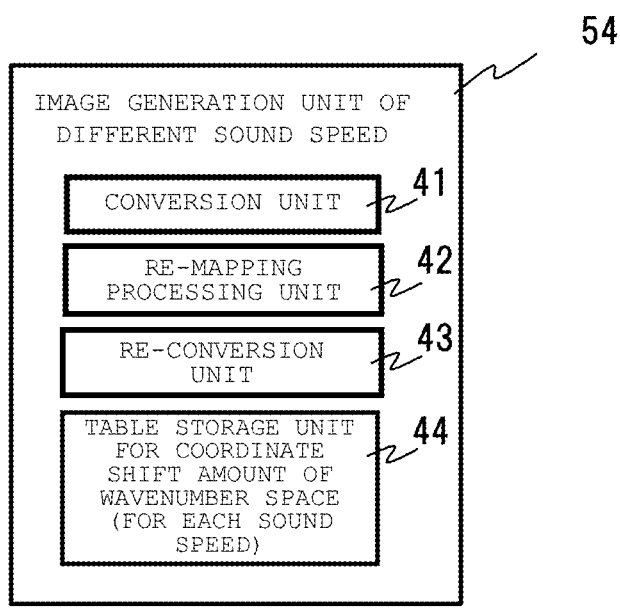
FIG. 15 is a block diagram showing a configuration of the image generation unit of different sound speed 54 of an ultrasound imaging device according to a fifth embodiment.
Figure 17:
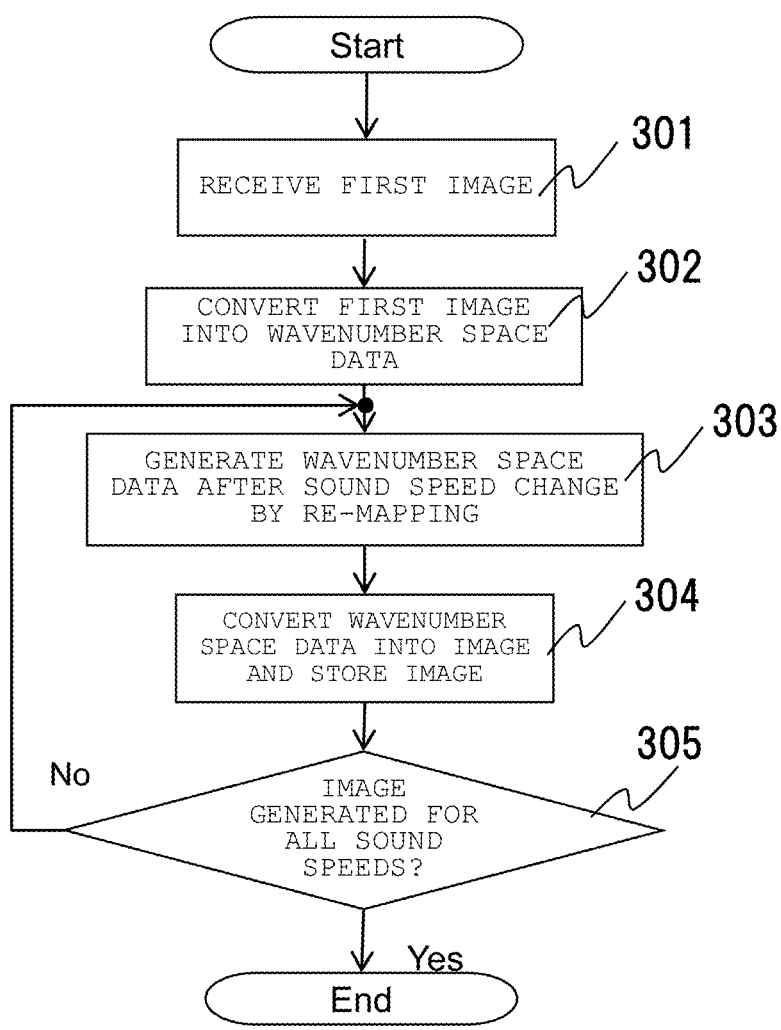
FIG. 17 is a flowchart showing processing operations of the image generation unit of different sound speed 54 according to the fourth embodiment.

An ultrasound imaging device according to a fifth embodiment will be described. FIG. 15 is a block diagram of the image generation unit of different sound speed 54 of the ultrasound imaging device according to the present embodiment. FIGS. 16A-16E are diagrams showing processing of the image generation unit of different sound speed 54. FIG. 17 is a flowchart showing processing of generating an image by calculation in the image generation unit of different sound speed 54.

In the first embodiment to the fourth embodiment, the image generation unit of different sound speed 54 causes the ultrasound image generation unit 52 to generate the plurality of types of images 61, 62, 63, and so on in which the sound speed for beamforming is changed into a plurality of types. In the fifth embodiment, the image generation unit of different sound speed 54 generates, by calculation, the plurality of types of images 61, 62, 63, and so on in which the sound speed for beamforming is changed into a plurality of types based on data of one type of image of the sound speed for beamforming generated by the ultrasound image generation unit 52.

Therefore, in the fifth embodiment, as shown in FIG. 15, the image generation unit of different sound speed 54 includes a conversion unit 41, a re-mapping processing unit 42, and a re-conversion unit 43.

Calculation processing of the image generation unit of different sound speed 54 will be described with reference to the flow in FIG. 17. The calculation processing of the image generation unit of different sound speed 54 is a known technique, and thus will be briefly described here.

Step 301

The image generation unit of different sound speed 54 receives data of a first image generated using a first delay time determined based on a first sound speed $C_0$ for beamforming from the ultrasound image generation unit 52 (FIG. 16A).

Step 302

The conversion unit 41 converts the data of the first image into first wavenumber space data in a wavenumber space (FIG. 16B).

The first image is a two-dimensional image on an x-z plane in which a direction of the row of the ultrasound probe elements 21 is the x direction and the depth direction of the imaging target 10 is the z direction. The conversion unit 41 converts the data of the first image into data in a two-dimensional wavenumber space having two axes of a wavenumber (kx) direction in the x direction and a wavenumber (kz) direction in the z direction.

Step 303

The re-mapping processing unit 42 processes the first wavenumber space data to generate data equivalent to second wavenumber space data obtained by converting a second image obtained when the received signals are processed with a second delay time determined based on a second sound speed for beamforming.

The second wavenumber space data is wavenumber space data obtained when the received signals (channel RF data) are processed with a second delay time $T_2$ (for example, $T_2=L/C_1$) determined based on a second sound speed $C_1$ and a distance L between reception focal points and the ultrasound probe element 21.

Coordinates $(kx_1, kz_1)$ of the second wavenumber space data have a predetermined relation represented using coordinates $(kx_0, kz_0)$ of the data constituting the first wavenumber space data and the sound speeds $C_0$, $C_1$. The image generation unit of different sound speed 54 stores, for example, in the form of a table, the relation between the coordinates $(kx_0, kz_0)$ of the data of the first wavenumber space and the corresponding coordinates $(kx_1, kz_1)$ when the coordinates are changed to the coordinates of the data in the case where the sound speed $C_1$ is phased with the second delay time T2 in a table storage unit 44 in advance (see FIG. 15).

The re-mapping processing unit 42 obtains, by interpolation calculation or the like, data values of sampling coordinates $(kx_1, kz_1)$ (coordinates of circles in FIG. 16C) shifted by a distance, which is obtained in advance based on the first sound speed $C_0$ and the second sound speed $C_1$, from the sampling coordinates $(kx_0, kz_0)$ of the data constituting the first wavenumber space data (FIG. 16B). When data obtained by interpolation calculation or the like is represented in a wavenumber space at the second sound speed $(C_1)$, sampling is performed at equal intervals (FIG. 16D).

Therefore, the re-mapping processing unit 42 reads the coordinates $(kx_1, kz_1)$ and the coordinates $(kx_0, kz_0)$ with reference to the table storage unit 44, calculates the data value of the coordinates $(kx_1, kz_1)$ of the first wavenumber space data by interpolation processing (FIG. 16C), and generates the second wavenumber space data (FIG. 16D) corresponding to the sound speed $C_1$.

Step 304

The re-conversion unit 43 performs inverse conversion on the data equivalent to the second wavenumber space data generated by the re-mapping processing unit 42 to generate a second image corresponding to the second sound speed $C_1$ (FIG. 16E). The obtained second image is data equivalent to an image obtained by phasing the received signals (channel RF data) with the second delay time T2 determined based on the second sound speed $C_1$.

Step 305

The image generation unit of different sound speed 54 repeats steps 303 and 304 until images are generated for all the predetermined sound speeds $C_2$ and $C_3$. The table storage unit 44 also stores information on coordinates to be calculated by interpolation in the first wavenumber space data for the plurality of sound speeds $C_2$ and $C_3$ other than the second sound speed $C_1$.

The image generation unit of different sound speed 54 stores the generated images corresponding to the sound speeds in the three-dimensional data set memory 58.

As described above, according to the ultrasound imaging device according to the fifth embodiment, by processing the generated image, it is possible to generate an image equivalent to an image in which the sound speed at the time of receive beamforming is changed with a small amount of calculation. Accordingly, by performing the subsequent processing in the same manner as in the first embodiment to the fourth embodiment, it is possible to generate, by estimation on the average sound speed or image processing, a high-quality image in which artifacts such as side lobes and grating lobes are prevented and the visibility of an actual signal of a structure in the imaging target 10 is improved.

As described above, according to the first embodiment to the fifth embodiment of the present disclosure, since pixels having high coherence can be extracted in units of pixels without performing correlation calculation on received signals between channels, it is possible to improve robustness and accuracy of sound speed estimation and to perform high-quality imaging with reduced artifacts and noise.

What is claimed is:

1. An ultrasound imaging device, comprising:
   a memory configured to store received signals from each of ultrasound probe elements, wherein the ultrasound probe elements are arranged in a row and the ultrasound probe elements transmit transmitted ultrasound waves and receive reflected ultrasound waves reflected by an imaging target of the transmitted ultrasound waves;
   an ultrasound image generation unit configured to perform receive beamforming processing of the received signals from the memory, using a delay time set based on a sound speed for beamforming, to generate an image in a predetermined imaging range;

an image generation unit of different sound speeds configured to cause the ultrasound image generation unit to generate a plurality of types of images in which the sound speed for beamforming is changed into a plurality of types of sound speeds, or to generate the plurality of types of images by calculation based on data of the image generated by the ultrasound image generation unit;

a coherence indicator calculation unit configured to arrange, in order of a plurality of sound speeds for beamforming, signal intensities of pixels at corresponding positions between the plurality of types of images having different sound speeds for beamforming, and generated by the image generation unit of different sound speeds, to obtain a change in the signal intensities in a direction associated with the sound speed for beamforming, and calculate a coherence indicator representing coherence of the received signals used for beamforming of the pixels based on the obtained change in the signal intensities, the coherence indicator calculation unit being further configured to calculate coherence indicators for the pixels in corresponding regions of interest (ROIs) of the plurality of types of images having the different sound speeds for beamforming, and an average sound speed estimation unit configured to estimate an average sound speed, which is an optimal sound speed for beamforming of the imaging target corresponding to a position of a pixel for which the coherence indicator is obtained, wherein the average sound speed estimation unit is further configured to estimate the average sound speed using a weighted sound speed that gives a maximum signal intensity obtained by weighting the sound speed that gives the maximum signal intensity using the calculated coherence indicators.

2. The ultrasound imaging device according to claim 1, wherein the average sound speed estimation unit is further configured to estimate the average sound speed using the coherence indicator and the signal intensities of the plurality of types of images having the different sound speeds for beamforming, set the estimated average sound speed as the sound speed for beamforming for the ultrasound image generation unit, and cause the ultrasound image generation unit to perform subsequent imaging.

3. The ultrasound imaging device according to claim 2, wherein the coherence indicator calculation unit is configured to calculate the coherence indicator for each of a plurality of pixels included in predetermined regions of interest (ROIs) in the predetermined imaging range, and the average sound speed estimation unit is configured to calculate a product of the coherence indicator and the signal intensities for each of the plurality of pixels for which the coherence indicator is calculated, and calculate a sum or an average value of the products in the predetermined ROIs as a focus index for each of the ROIs corresponding to the plurality of types of images having the different sound speeds for beamforming, and obtain an image of which the obtained focus index is maximum, and estimate the sound speed for beamforming of the obtained image as the average sound speed.

4. The ultrasound imaging device according to claim 2, further comprising:

a sound speed that gives a maximum signal intensity calculation unit configured to compare the signal intensities of the pixels in the corresponding regions of interest (ROIs) of the plurality of types of images having the different sound speeds for beamforming with each other among the pixels at the corresponding positions of the plurality of types of images to select an image having a maximum signal intensity, and obtain the sound speed for beamforming of the selected image as a sound speed that gives the maximum signal intensity at the positions of the pixels.

5. The ultrasound imaging device according to claim 4, wherein the coherence indicator calculation unit and the sound speed that gives the maximum signal intensity calculation unit are configured to calculate the coherence indicators and maximum signal intensity acquisition sound speeds for the pixels in the ROIs, respectively, and the average sound speed estimation unit is configured to obtain the weighted sound speed that gives the maximum signal intensity for the pixels in the ROIs, and set an average value of the weighted sound speed that gives the maximum signal intensity as the average sound speed.

6. The ultrasound imaging device according to claim 5, wherein the coherence indicator calculation unit is configured to obtain a distribution of the coherence indicators in the ROIs, the sound speed that gives the maximum signal intensity calculation unit is configured to obtain a distribution of the sound speeds that give the maximum signal intensity in the ROIs, and the average sound speed estimation unit is configured to obtain a distribution of the weighted sound speeds that gives the maximum signal intensity by weighting the distribution of the sound speeds that give the maximum signal intensity in the ROIs by the distribution of the coherence indicators in the ROIs, and set an average value of the distribution of the weighted sound speeds that give the maximum signal intensity as the average sound speed.

7. The ultrasound imaging device according to claim 1, further comprising:

an image processing unit configured to generate a processed image using the coherence indicator and the signal intensities of one or more of the plurality of types of images having the different sound speeds for beamforming.

8. The ultrasound imaging device according to claim 7, wherein the coherence indicator calculation unit is configured to calculate coherence indicators for a plurality of pixels included in the predetermined imaging range to obtain a distribution of the coherence indicators in the plurality of types of images having the different sound speeds for beamforming, and the image processing unit is configured to generate the processed image by performing image processing on one or more images among the plurality of types of images having the different sound speeds for beamforming such that a signal intensity of a first region having a high coherence indicator is larger than a signal intensity of a second region having lower coherence than that of the first region.

9. The ultrasound imaging device according to claim 8, wherein the image processing by the image processing unit is performed on one image of the plurality of types of images having the different sound speeds, to generate the processed image.

10. The ultrasound imaging device according to claim 9, wherein
the one image on which the image processing is performed is an image having a predetermined specified sound speed among the plurality of types of images having the different sound speeds.

11. The ultrasound imaging device according to claim 9, wherein
the one image on which the image processing unit performs the image processing is an image having the average sound speed estimated for predetermined regions of interest (ROIs) among the plurality of types of images having the different sound speeds.

12. The ultrasound imaging device according to claim 8, wherein
the image processing unit is configured to generate the processed image by performing weighted addition of the signal intensities of the pixels at the corresponding positions of the plurality of types of images having the different sound speeds for beamforming.

13. The ultrasound imaging device according to claim 12, further comprising:
a sound speed that gives the maximum signal intensity calculation unit, wherein
the sound speed that gives the maximum signal intensity calculation unit is configured to compare the signal intensities of the pixels at the corresponding positions of the plurality of types of images having the different sound speeds for beamforming with each other among the plurality of types of images, select an image having a maximum signal intensity, and obtain the sound speed for beamforming of the selected image as the sound speed that gives the maximum signal intensity at the positions of the pixels to obtain a distribution of the sound speeds that give the maximum signal intensity, and
the image processing unit is configured to set a weight of the signal intensity of the image in which the sound speed that gives the maximum signal intensity at the time of weighting is set as the sound speed for beamforming such that the weight of the signal intensity of the image increases as the coherence indicator increases.

14. The ultrasound imaging device according to claim 13, further comprising:
a minimum signal intensity acquisition sound speed calculation unit, wherein
the minimum signal intensity acquisition sound speed calculation unit is configured to compare the signal intensities of the pixels at the corresponding positions of the plurality of types of images having the different sound speeds for beamforming with each other among the plurality of types of images, select an image having a minimum signal intensity, and set the sound speed for beamforming of the selected image as a minimum signal intensity acquisition sound speed at the positions of the pixels, and
at the time of weighting, the image processing unit is configured to set the weight of the signal intensity of the image in which the sound speed that gives the maximum signal intensity is set as the sound speed for beamforming for a pixel having a coherence value larger than a predetermined value to be larger than a weight of a signal intensity of the selected image in which the minimum signal intensity acquisition sound speed is set as the sound speed for beamforming, and set the weight of the signal intensity of the image in which the minimum signal intensity acquisition sound speed is set as the sound speed for beamforming for a pixel having a coherence value smaller than a predetermined value to be larger than the weight of the signal intensity of the image in which the sound speed that gives the maximum signal intensity is set as the sound speed for beamforming.

15. The ultrasound imaging device according to claim 1, wherein the coherence indicator calculation unit is configured to
generate a graph representing the change in the signal intensities of corresponding pixels of the plurality of types of images having the different sound speeds for beamforming, a horizontal axis representing the sound speed for beamforming and a vertical axis representing a magnitude of the signal intensities, obtain a curve representing the change in the signal intensities,
calculate at least one feature amount among whether the curve has an upward convex shape, a change amount of the curve, an approximation accuracy of the curve to a predetermined polynomial, and a local extreme value of the curve, and
calculate the coherence indicator from the at least one feature amount.

16. The ultrasound imaging device according to claim 1, wherein
the image generation unit of different sound speeds is configured to cause the ultrasound image generation unit to set the sound speed for beamforming for each image and to sequentially generate the plurality of types of images having the different sound speeds for beamforming.

17. The ultrasound imaging device according to claim 1, wherein
the ultrasound image generation unit includes a plurality of receive beamformers configured to perform beamforming processing on the received signals, and
the image generation unit of different sound speeds is configured to cause the plurality of receive beamformers to set delay times of the plurality of types of the plurality of sound speeds for beamforming, and cause the plurality of receive beamformers to perform the beamforming processing in parallel for a same scan line, thereby generating the plurality of types of images in parallel.

18. The ultrasound imaging device according to claim 1, wherein the image generation unit of different sound speeds includes a conversion unit configured to convert data of a first image generated by the ultrasound image generation unit using a first delay time determined based on a first sound speed for beamforming into first wavenumber space data in a wavenumber space, a re-mapping processing unit configured to generate, by processing the first wavenumber space data, data equivalent to second wavenumber space data, and a re-conversion unit configured to generate a second image by performing inverse conversion on the data equivalent to the second wavenumber space data generated by the re-mapping processing unit, wherein the second wavenumber space data is obtained by converting the second image obtained when the received signals are processed with a second delay time determined based on a second sound speed for beamforming.

19. The ultrasound imaging device according to claim 1, wherein
the image generation unit of different sound speeds is configured to generate a three-dimensional data set by arranging the images obtained when the sound speed for beamforming is changed to a plurality of types in the direction associated with the sound speed for beamforming, and
the coherence indicator calculation unit is configured to obtain, in the three-dimensional data set, the change in the signal intensities in the direction associated with the sound speed for beamforming for one or more pixels among the pixels constituting the image and calculate one or more coherence indicators.

20. A signal processing device, comprising:
a memory configured to store, received from the outside, received signals from each of ultrasound probe elements, wherein the ultrasound probe elements are arranged in a row and the ultrasound probe elements transmit transmitted ultrasound waves and receive reflected ultrasound waves reflected by an imaging target of the transmitted ultrasound waves;
an ultrasound image generation unit configured to perform receive beamforming processing of the received signals from the memory, using a delay time set based on a sound speed for beamforming, to generate an image in a predetermined imaging range;
an image generation unit of different sound speeds configured to cause the ultrasound image generation unit to generate a plurality of types of images in which the sound speed for beamforming is changed into a plurality of types of sound speeds, or to generate the plurality of types of images by calculation based on data of the image generated by the ultrasound image generation unit; a coherence indicator calculation unit configured to arrange, in order of a plurality of sound speeds for beamforming, signal intensities of pixels at corresponding positions between the plurality of types of images having different sound speeds for beamforming, and generated by the image generation unit of different sound speeds, to obtain a change in the signal intensities in a direction associated with the sound speed for beamforming, and calculate a coherence indicator representing coherence of the received signals used for beamforming of the pixels based on the obtained change in the signal intensities, the coherence indicator calculation unit being further configured to calculate coherence indicators for the pixels in corresponding regions of interest (ROIs) of the plurality of types of images having the different sound speeds for beamforming; and an average sound speed estimation unit configured to estimate an average sound speed, which is an optimal sound speed for beamforming of the imaging target corresponding to a position of a pixel for which the coherence indicator is obtained,
wherein the average sound speed estimation unit is further configured to estimate the average sound speed using a weighted sound speed that gives a maximum signal intensity obtained by weighting the sound speed that gives the maximum signal intensity using the calculated coherence indicators.

21. A signal processing method comprising:
storing, received from the outside, received signals from each of ultrasound probe elements, wherein the ultrasound probe elements are arranged in a row and the ultrasound probe elements transmit transmitted ultrasound waves and receive reflected ultrasound waves reflected by an imaging target of the transmitted ultrasound waves;
performing receive beamforming processing of the received signals, by using a delay time set based on a sound speed for beamforming to generate an image in a predetermined imaging range;
generating a plurality of types of the images in which the sound speed for beamforming is changed into a plurality of types of sound speeds by the receive beamforming processing, or by calculation based on data of the generated image;
obtaining a change in signal intensities in a direction associated with the sound speed for beamforming by arranging, in order of a plurality of sound speeds for beamforming, the signal intensities of pixels at corresponding positions between the plurality of types of images having different sound speeds for beamforming, and calculating a coherence indicator representing coherence of the received signals used for beamforming of the pixels based on the obtained change in the signal intensities;
calculating coherence indicators for the pixels in corresponding regions of interest (ROIs) of the plurality of types of images having the different sound speeds for beamforming; and
estimating an average sound speed, which is an optimal sound speed for beamforming of the imaging target corresponding to a position of a pixel for which the coherence indicator is obtained,
the average sound speed being estimated using a weighted sound speed that gives a maximum signal intensity obtained by weighting the sound speed that gives the maximum signal intensity using the calculated coherence indicators.

* * * * *